US011375167B2

(12) United States Patent
Michihata et al.

(10) Patent No.: US 11,375,167 B2
(45) Date of Patent: Jun. 28, 2022

(54) IMAGE PROCESSING APPARATUS AND OBSERVATION SYSTEM

(71) Applicants: Sony Olympus Medical Solutions Inc., Tokyo (JP); Sony Corporation, Tokyo (JP)

(72) Inventors: Taihei Michihata, Kanagawa (JP); Satoshi Mitsui, Aichi (JP)

(73) Assignees: SONY OLYMPUS MEDICAL SOLUTIONS INC., Tokyo (JP); SONY CORPORATION, Tokyo (JP)

( * ) Notice: Subject to any disclaimer, the term of this patent is extended or adjusted under 35 U.S.C. 154(b) by 0 days.

(21) Appl. No.: 16/720,011

(22) Filed: Dec. 19, 2019

(65) Prior Publication Data

US 2020/0221059 A1 Jul. 9, 2020

(30) Foreign Application Priority Data

Jan. 7, 2019 (JP) .............................. JP2019-000843

(51) Int. Cl.
*H04N 9/73* (2006.01)
*A61B 1/00* (2006.01)
*H04N 9/64* (2006.01)

(52) U.S. Cl.
CPC ......... *H04N 9/735* (2013.01); *A61B 1/00004* (2013.01); *A61B 1/00149* (2013.01); *H04N 9/646* (2013.01)

(58) Field of Classification Search
CPC .............................. H04N 9/735; A61B 1/0004
See application file for complete search history.

(56) References Cited

U.S. PATENT DOCUMENTS

| | | | | |
|---|---|---|---|---|
| 2002/0039142 A1* | 4/2002 | Zhang | ...................... | G06T 5/20 348/234 |
| 2004/0051790 A1* | 3/2004 | Tamaru | .................. | H04N 5/235 348/223.1 |
| 2004/0105017 A1* | 6/2004 | Aotsuka | ................. | H04N 5/772 348/223.1 |
| 2007/0153542 A1* | 7/2007 | Gono | ................... | A61B 1/0669 362/574 |
| 2010/0002104 A1* | 1/2010 | On | .......................... | G06T 5/007 348/252 |
| 2014/0125828 A1* | 5/2014 | Takeuchi | ............. | H04N 5/2254 348/208.99 |
| 2015/0326842 A1* | 11/2015 | Huai | ...................... | H04N 9/646 348/223.1 |
| 2017/0366723 A1* | 12/2017 | Kurata | ............... | H04N 9/04553 |

FOREIGN PATENT DOCUMENTS

JP 2013-179400 A 9/2013

\* cited by examiner

*Primary Examiner* — Zhubing Ren
(74) *Attorney, Agent, or Firm* — Xsensus LLP

(57) ABSTRACT

An image processing apparatus includes a processor including hardware. The processor is configured to: execute a first white balance adjustment on a first signal corresponding to multiple wavelength bands; generate a luminance signal from a second signal including an area having saturation caused by the first white balance adjustment; extract a detail component based on the first signal; and apply the detail component to the luminance signal to generate a corrected luminance signal.

11 Claims, 16 Drawing Sheets

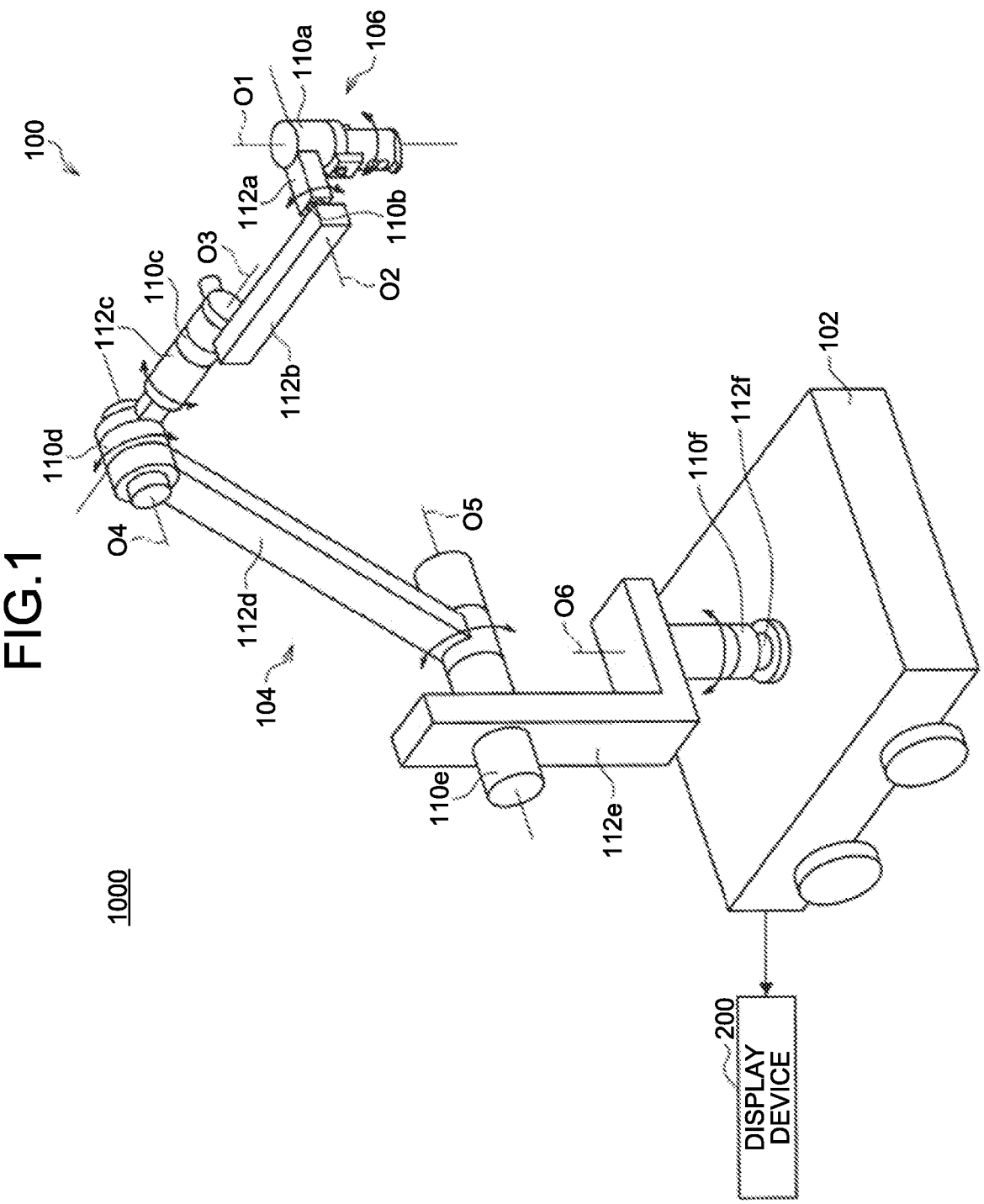

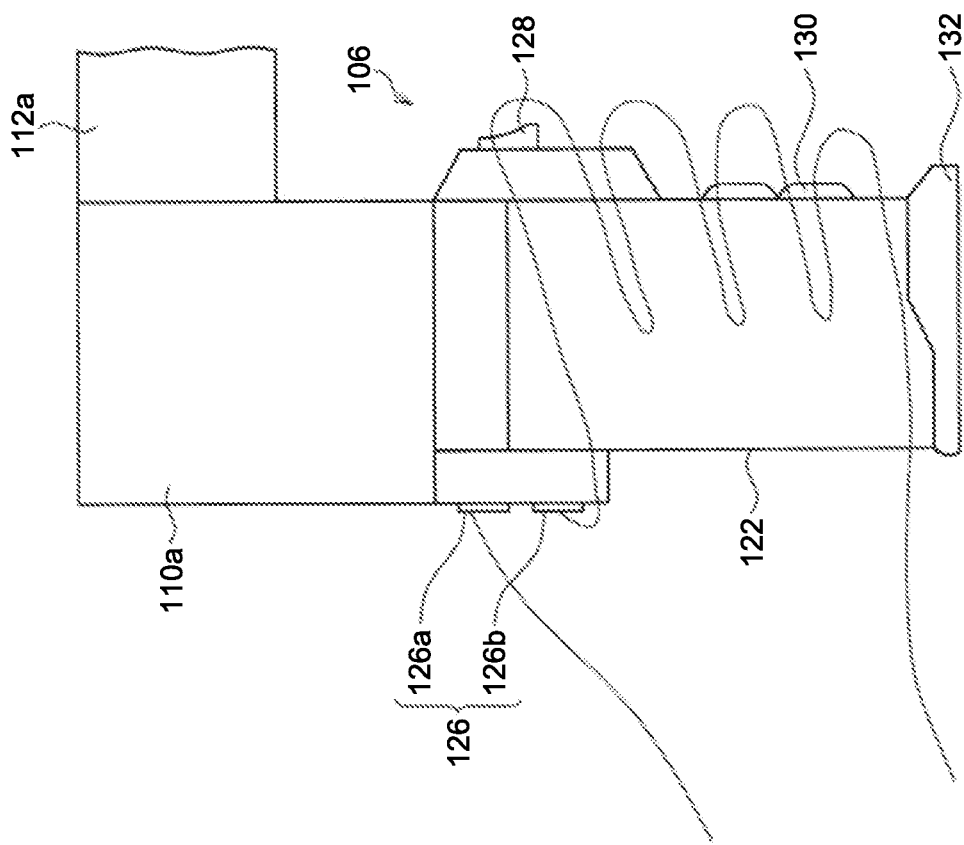
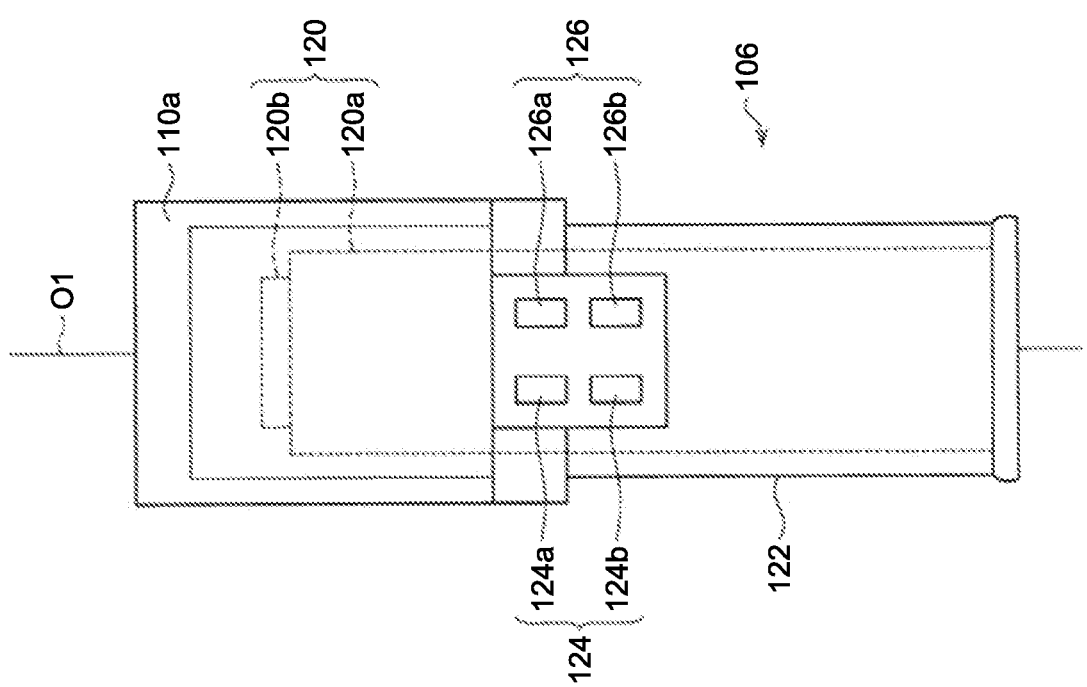
FIG.2B
FIG.2A

FIG.5
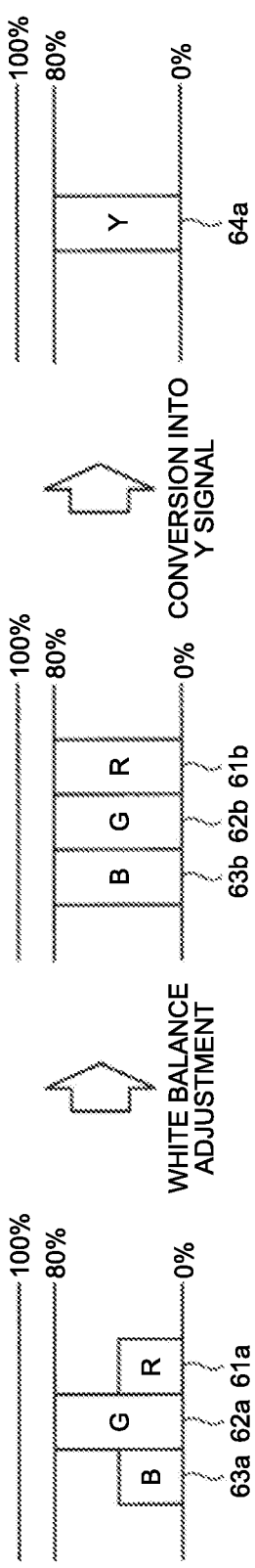
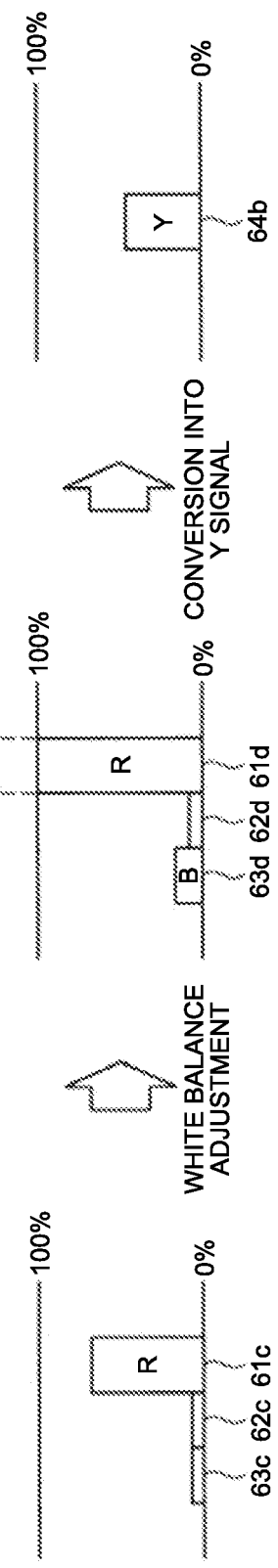

IMAGE PROCESSING APPARATUS AND OBSERVATION SYSTEM

This application claims the benefit of Japanese Priority Patent Application JP 2019-000843 filed Jan. 7, 2019, the entire contents of which are incorporated herein by reference.

BACKGROUND

The present disclosure relates to an image processing apparatus and an observation system.

Typically, imaging devices such as digital cameras may perform, as one type of image processing, a process to adjust the white balance to correct the color. Due to the adjustment on the white balance, there may be a phenomenon called the color phase shift, which is the shift in a color phase of the color of the imaging target appearing in the captured image. When the color phase shift occurs, the imaging target appearing in the captured image may be displayed in a color different from the original color of the imaging target. For this reason, the technique has been developed to correct the color at the area where the color phase shift has occurred.

For example, Japanese Laid-open Patent Publication No. 2013-179400 discloses the technique for detecting, from the image data, the pixel of which the tone value indicating the color component reaches the saturation level and correcting the tone value of the color component of the detected pixel.

SUMMARY

The technique disclosed in Japanese Laid-open Patent Publication No. 2013-179400 makes it possible to correct the tone value of the color component of the detected pixel so as to prevent the color phase shift. However, no consideration is given to the restoration of the lost detail of the captured image due to the occurrence of the color saturation after the tone value reaches the saturation level.

There is a need for an image processing apparatus and an observation system that are new and improved so as to restore the detail of the area having saturation.

According to one aspect of the present disclosure, there is provided an image processing apparatus including a processor including hardware, the processor being configured to: execute a first white balance adjustment on a first signal corresponding to multiple wavelength bands; generate a luminance signal from a second signal including an area having saturation caused by the first white balance adjustment; extract a detail component based on the first signal; and apply the detail component to the luminance signal to generate a corrected luminance signal.

According to another aspect of the present disclosure, there is provided an observation system including: an imager configured to capture an imaging target; and an image processing apparatus including a processor including hardware, the processor being configured to: execute a white balance adjustment on a first signal corresponding to multiple wavelength bands; generate a luminance signal from a second signal including an area having saturation caused by the white balance adjustment; extract a detail component based on the first signal; and apply the detail component to the luminance signal to generate a corrected luminance signal.

BRIEF DESCRIPTION OF THE DRAWINGS

FIG. 1 is a diagram that illustrates a first example of the external configuration of a medical observation system according to an embodiment;

FIG. 2A and FIG. 2B are diagrams that illustrate an example of the external configuration of an imaging device included in a medical observation device according to the embodiment;

FIG. 5 is a diagram that illustrates an example of the image processing;

DETAILED DESCRIPTION

Figure 3:
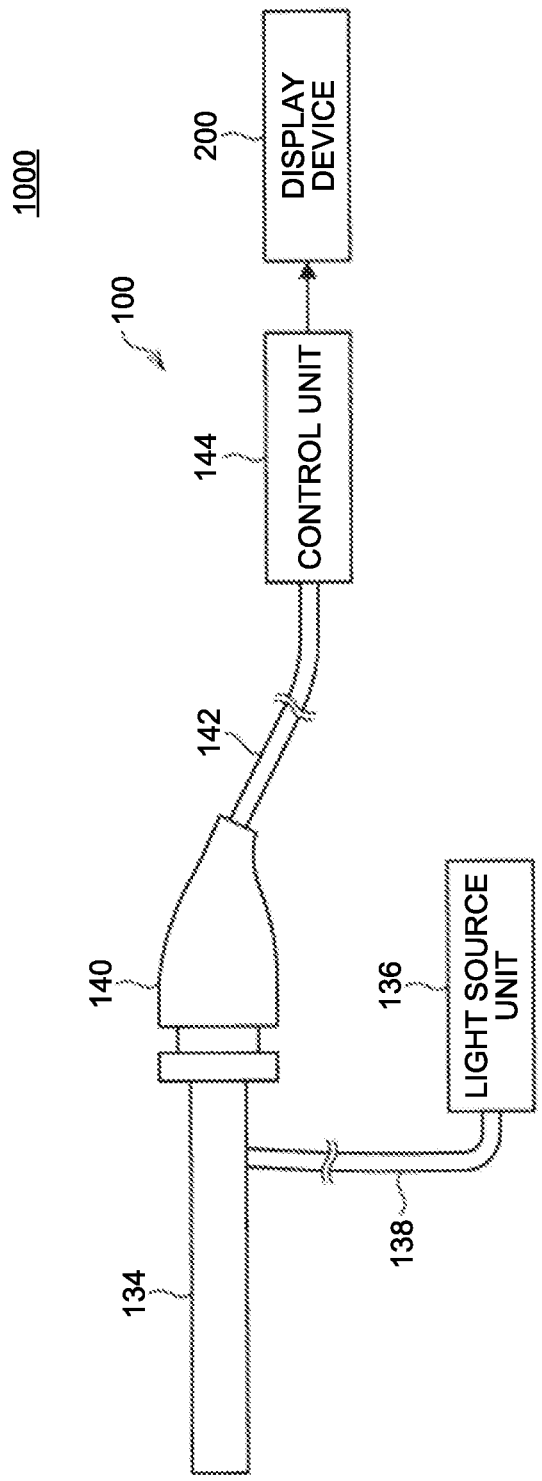
FIG. 3 is a diagram that illustrates a second example of the external configuration of the medical observation system according to the embodiment.

With reference to the accompanying drawings, a preferred embodiment is described below in detail. In the descriptions and the drawings, the components having substantially the same functional configuration are denoted by the same reference numeral, and duplicated descriptions are omitted.

In the descriptions and the drawings, the components having substantially the same functional configuration may be denoted by the same reference numeral followed by different alphabets so as to be discriminated from each other. For example, the components having substantially the same functional configuration are distinguished from each other as appropriate, e.g., an image processing unit 180*a* and an image processing unit 180*b*. When the components having substantially the same functional configuration are not particularly distinguished from each other, they are simply denoted by the same reference numeral. For example, when the image processing unit 180*a* and the image processing unit 180*b* are not particularly distinguished, they are simply referred to as an image processing unit 180.

The descriptions are given in the following order.

1. External configuration of an observation system according to an embodiment
   - 1-1. The observation system according to a first example
   - 1-2. The observation system according to a second example
   - 1-3. The observation system according to another example
2. Functional configuration of an observation device according to an embodiment
3. An image processing unit according to a first embodiment
   - 3-1. Functional configuration of the image processing unit
   - 3-2. Flow of image processing
4. An image processing unit according to a second embodiment
   - 4-1. Functional configuration of the image processing unit
   - 4-2. Flow of image processing
5. An image processing unit according to a third embodiment
   - 5-1. Functional configuration of the image processing unit
   - 5-2. Flow of image processing
6. An image processing unit according to a fourth embodiment
   - 6-1. Functional configuration of the image processing unit
   - 6-2. Flow of image processing
   - 6-3. Modification
7. An image processing unit according to a fifth embodiment
   - 7-1. Functional configuration of the image processing unit
   - 7-2. Flow of image processing
   - 7-3. Modification
8. Modification
9. Hardware configuration example
10. Conclusion

1. External Configuration of an Observation System According to an Embodiment First, an external configuration of an observation system according to an embodiment is described. In the case principally described below, an observation device according to the present embodiment includes an image processing apparatus according to the present embodiment, and the observation device performs image processing. The device including the image processing apparatus in the observation system according to the present embodiment is not limited to the observation device according to the present embodiment. For example, in the observation system according to the present embodiment, a display device described later may include the image processing apparatus according to the present embodiment. In the observation system according to the present embodiment, any device, such as a medical controller, capable of executing image processing may include the image processing apparatus.

1-1. The Observation System According to a First Example

First, as a first example of the observation system, an example of a medical observation system, which is an observation system used in the medical fields, is described. FIG. 1 is a diagram that illustrates the first example of the external configuration of a medical observation system 1000 according to the embodiment. As illustrated in FIG. 1, the medical observation system 1000 includes, for example, a medical observation device 100 and a display device 200. The medical observation system 1000 according to the first example is not limited to the example illustrated in FIG. 1.

For example, the medical observation system 1000 according to the first example may further include a control device (not illustrated) that controls various types of operations of the medical observation device 100. In the example illustrated in FIG. 1, in the medical observation system 1000, as described later, the medical observation device 100 includes a control unit (described later) so that the medical observation device 100 has the function as the control device (not illustrated). Examples of the control device (not illustrated) include "a medical controller" or "a computer such as a server". The control device (not illustrated) may be an integrated circuit (IC) that is installable in the above-described device.

The medical observation system 1000 according to the first example may include the medical observation devices 100 or the display devices 200 or both. When the medical observation devices 100 are included, each of the medical observation devices 100 performs the image processing described later. When the medical observation system 1000 according to the first example includes the medical observation devices 100 and the display devices 200, the medical observation devices 100 and the display devices 200 may be related to each other on a one-to-one basis, or the medical observation devices 100 may be related to the single display device 200. When the medical observation devices 100 are related to the single display device 200, the display device 200 performs, for example, a selection operation to select the image captured by one of the medical observation devices 100 so as to be displayed on the display screen.

(1) The Display Device 200

The display device 200 is a display unit in the medical observation system 1000 according to the first example and corresponds to an external display device for the medical observation device 100. The display device 200 displays, on the display screen, various images such as a medical-use captured image, which is captured by the medical observation device 100, and an image related to a user interface (UI). The display device 200 may be configured to enable the 3D display by using any method. The display on the display device 200 is controlled by, for example, the medical observation device 100 or the control device (not illustrated).

In the medical observation system 1000, the display device 200 is provided at any place, such as a wall surface, a ceiling, or a floor surface of the operation room, which may be viewed by a person such as an operator involved in a surgery within the operation room.

Examples of the display device 200 include a liquid crystal display, an organic electro-luminescence (EL) display, or a cathode ray tube (CRT) display. The display device 200 is not limited to the above-described examples. For example, the display device 200 may be any wearable devices, such as a head-mounted display or an eyewear device, which may be attached to the operator' body, or the like, while in use.

The display device 200 is driven with, for example, the electric power supplied from an internal power source, such as a battery, included in the display device 200 or the electric power supplied from an externally connected power source.

(2) The Medical Observation Device 100

The medical observation device 100 illustrated in FIG. 1 is a medical electronic observation device. For example, when the medical observation device 100 illustrated in FIG. 1 is used during a surgery, the operator (an example of the user of the medical observation device 100) observes a surgery site (diseased site) while checking the medical-use captured image that is captured by the medical observation device 100 and displayed on the display screen of the display device 200 to perform various treatments, such as the procedure corresponding to a surgical method, on the surgery site. As illustrated in FIG. 1, the medical observation device 100 includes, for example, a base 102, an arm 104, and an imaging device 106.

Although not illustrated in FIG. 1, the medical observation device 100 may include one or more processors (not illustrated) including an arithmetic circuit such as a micro processing unit (MPU), a read only memory (ROM) (not illustrated), a random access memory (RAM) (not illustrated), a recording medium (not illustrated), and a communication device (not illustrated). The medical observation device 100 is driven with, for example, the electric power supplied from an internal power source, such as a battery, included in the medical observation device 100 or the electric power supplied from an externally connected power source.

A processor (not illustrated) functions as a control unit (described later) in the medical observation device 100. The ROM (not illustrated) stores control data, such as programs and calculation parameters used by the processor (not illustrated). The RAM (not illustrated) temporarily stores programs, and the like, executed by the processor (not illustrated).

The recording medium (not illustrated) functions as a storage unit (not illustrated) in the medical observation device 100. The recording medium (not illustrated) stores data regarding image processing according to the present embodiment and various types of data for various applications. Examples of the recording medium (not illustrated) include a magnetic recording medium, such as a hard disk, or a nonvolatile memory such as a flash memory. The recording medium (not illustrated) may be attached to and detached from the medical observation device 100.

The communication device (not illustrated) is a communication unit included in the medical observation device 100 to provide the function to communicate with an external device, such as the display device 200, wirelessly or via a wired line. Examples of the communication device (not illustrated) include an IEEE 802.15.1 port and a transmission/reception circuitry (wireless communication), an IEEE 802.11 port and a transmission/reception circuitry (wireless communication), a communication antenna and an RF circuitry (wireless communication), or a LAN terminal and a transmission/reception circuitry (wired communication).

(2-1) The Base 102

The base 102 is the base of the medical observation device 100 and is coupled to one end of the arm 104 so as to support the arm 104 and the imaging device 106. The base 102 is provided with, for example, casters so that the medical observation device 100 is in contact with the floor surface via the casters. As the casters are provided, the medical observation device 100 may easily move on the floor surface with the casters.

(2-2) The Arm 104

The arm 104 is configured such that links are coupled to one another via joint parts. The arm 104 supports the imaging device 106. The imaging device 106 supported by the arm 104 is movable in three dimensions and, after the imaging device 106 is moved, the position and the posture of the imaging device 106 are maintained by the arm 104.

More specifically, the arm 104 includes, for example, a plurality of joint parts 110*a*, 110*b*, 110*c*, 110*d*, 110*e*, and 110*f* and a plurality of links 112*a*, 112*b*, 112*c*, 112*d*, 112*e*, and 112*f* that are rotatably coupled to one another via the joint parts 110*a*, 110*b*, 110*c*, 110*d*, 110*e*, and 110*f*. The rotatable range of each of the joint parts 110*a*, 110*b*, 110*c*, 110*d*, 110*e*, and 110*f* is optionally set at the design stage, the manufacturing stage, etc. so as to enable the desired movement of the arm 104.

Specifically, in the medical observation device 100 illustrated in FIG. 1, six rotation axes (a first axis O1, a second axis O2, a third axis O3, a fourth axis O4, a fifth axis O5, and a sixth axis O6) corresponding to the six joint parts 110*a*, 110*b*, 110*c*, 110*d*, 110*e*, and 110*f* included in the arm 104 enable six degrees of freedom with regard to the movement of the imaging device 106. More specifically, the medical observation device 100 illustrated in FIG. 1 enables three degrees of freedom in translation and three degrees of freedom in rotation, that is, six degrees of freedom in movement.

Each of the joint parts 110*a*, 110*b*, 110*c*, 110*d*, 110*e*, and 110*f* is provided with an actuator (not illustrated) so that each of the joint parts 110*a*, 110*b*, 110*c*, 110*d*, 110*e*, and 110*f* is rotated around the corresponding rotation axis due to the driving of the actuator (not illustrated). The driving of the actuator (not illustrated) is controlled by, for example, a processor functioning as a control unit described later or an external control device (not illustrated).

Each of the joint parts 110*a*, 110*b*, 110*c*, 110*d*, 110*e*, and 110*f* may be provided with an angle sensor (not illustrated) capable of detecting the rotation angle with respect to the six rotation axes. Examples of the angle sensor include any sensor, such as a rotary encoder or an angular velocity sensor, which may obtain the rotation angle with respect to the six rotation axes.

Each of the joint parts 110*a*, 110*b*, 110*c*, 110*d*, 110*e*, and 110*f* is rotated around the corresponding rotation axis due to the driving of the actuator (not illustrated) so as to enable various movements of the arm 104, such as the stretching, shortening (folding), and the like, of the arm 104.

The joint part 110*a* has substantially a cylindrical shape, and the distal end part (the lower end part in FIG. 1) of the joint part 110*a* supports the imaging device 106 (the upper end part of the imaging device 106 in FIG. 1) so as to rotate the imaging device 106 around the rotation axis (the first axis O1) parallel to the central axis of the imaging device 106. The medical observation device 100 is configured such that the first axis O1 matches the optical axis of the imaging device 106. That is, when the imaging device 106 is rotated around the first axis O1 illustrated in FIG. 1, the medical-use captured image captured by the imaging device 106 is changed such that the field of view thereof is rotated.

The link 112*a* is a member having substantially a rod-like shape to fixedly support the joint part 110*a*. The link 112*a* extends, for example, in a direction perpendicular to the first axis O1 to be coupled to the joint part 110*b*.

The joint part 110*b* has substantially a cylindrical shape to support the link 112*a* such that the link 112*a* is rotatable around the rotation axis (the second axis O2) perpendicular to the first axis O1. The link 112*b* is fixedly coupled to the joint part 110*b*.

The link 112*b* is a member having substantially a rod-like shape and extends in a direction perpendicular to the second axis O2. The link 112*b* is coupled to the joint part 110*b* and the joint part 110*c*.

The joint part 110*c* has substantially a cylindrical shape to support the link 112*b* such that the link 112*b* is rotatable around the rotation axis (the third axis O3) perpendicular to the first axis O1 and the second axis O2. The joint part 110*c* is fixedly coupled to one end of the link 112*c*.

As the distal end side (the side on which the imaging device 106 is provided) of the arm 104 is rotated around the second axis O2 and the third axis O3, the imaging device 106 is movable such that the position of the imaging device 106 may be changed within the horizontal plane. That is, in the medical observation device 100, as the rotation around the second axis O2 and the third axis O3 is controlled so that the field of view of a medical-use captured image is movable on the plane.

The link 112c is a member having substantially a cylindrical shape at one end and having substantially a rod-like shape at the other end. One end side of the link 112c is fixedly coupled to the joint part 110c such that the central axis of the joint part 110c is identical to the central axis of the substantially cylindrical shape. The other end side of the link 112c is coupled to the joint part 110d.

The joint part 110d has substantially a cylindrical shape to support the link 112c such that the link 112c is rotatable around the rotation axis (the fourth axis O4) perpendicular to the third axis O3. The joint part 110d is fixedly coupled to the link 112d.

The link 112d is a member having substantially a rod-like shape and extends so as to run at right angles to the fourth axis O4. One end of the link 112d is fixedly coupled to the joint part 110d so as to abut the side surface of the substantially cylindrical shape of the joint part 110d. The other end of the link 112d (the end thereof at the opposite side of the side where the joint part 110d is coupled) is coupled to the joint part 110e.

The joint part 110e has substantially a cylindrical shape to support one end of the link 112d such that the link 112d is rotatable around the rotation axis (the fifth axis O5) parallel to the fourth axis O4. The joint part 110e is fixedly coupled to one end of the link 112e.

The fourth axis O4 and the fifth axis O5 are rotation axes for moving the imaging device 106 in a vertical direction. As the distal end side (the side where the imaging device 106 is provided) of the arm 104 is rotated around the fourth axis O4 and the fifth axis O5, the position of the imaging device 106 is changed in the vertical direction. Thus, as the distal end side (the side where the imaging device 106 is provided) of the arm 104 is rotated around the fourth axis O4 and the fifth axis O5, the distance between the imaging device 106 and the imaging target may be changed. The imaging target is the observation target, such as a surgery site of the patient. Hereafter, the imaging target is also referred to as the observation target.

The link 112e is a member combining a first member having substantially an L-shape in which one side thereof extends in a vertical direction and the other side thereof extends in a horizontal direction and a second member having a rod-like shape and extending downward in the vertical direction from the part of the first member extending in the horizontal direction. The part of the first member of the link 112e extending in the vertical direction is fixedly coupled to the joint part 110e. The second member of the link 112e is coupled to the joint part 110f.

The joint part 110f has substantially a cylindrical shape to support the link 112e such that the link 112e is rotatable around the rotation axis (the sixth axis O6) parallel to the vertical direction. The joint part 110f is fixedly coupled to the link 112f.

The link 112f is a member having substantially a rod-like shape and extending in the vertical direction. One end of the link 112f is coupled to the joint part 110f. The other end (the end at the opposite side of the side where the joint part 110f is coupled) of the link 112f is fixedly coupled to the base 102. As the arm 104 has the above-described configuration, the medical observation device 100 enables six degrees of freedom with regard to the movement of the imaging device 106.

The configuration of the arm 104 is not limited to the example described above. For example, each of the joint parts 110a, 110b, 110c, 110d, 110e, and 110f of the arm 104 may be provided with a brake for restricting the rotation of the joint parts 110a, 110b, 110c, 110d, 110e, and 110f. The brake according to the present embodiment may be any type of brake, such as a brake for the mechanical driving or an electromagnetic brake for electrical driving.

The driving of the above-described brake is controlled by, for example, a processor functioning as the control unit described later or an external control device (not illustrated). By controlling the driving of the above-described brake, in the medical observation device 100, an operation mode of the arm 104 is set. Examples of the operation mode of the arm 104 include a fixed mode and a free mode.

The fixed mode according to the present embodiment is, for example, an operation mode in which the rotation at each rotation axis provided in the arm 104 is restricted by the brake so that the position and the posture of the imaging device 106 are fixed. When the arm 104 is in the fixed mode, the operating state of the medical observation device 100 is the fixed state in which the position and the posture of the imaging device 106 are fixed.

The free mode according to the present embodiment is an operation mode in which the above-described brake is released so that the free rotation is enabled at each rotation axis provided in the arm 104. For example, in the free mode, the position and the posture of the imaging device 106 may be adjusted by the direct operation of the operator. The direct operation according to the present embodiment refers to, for example, the operation to directly move the imaging device 106 by the operator who grasps the imaging device 106 with the hand.

(2-3) The Imaging Device 106

The imaging device 106 is a device that is supported by the arm 104 to capture the imaging target. For example, the imaging device 106 captures the observation target such as a surgery site of the patient. The imaging of the imaging device 106 is controlled by, for example, the processor functioning as the control unit described later or an external control device (not illustrated). The imaging device 106 has the configuration that is equivalent to, for example, an electronic microscope.

FIG. 2A and FIG. 2B are diagrams that illustrate an example of the external configuration of the imaging device 106 included in the medical observation device 100 according to the embodiment. As illustrated in FIG. 2A and FIG. 2B, the imaging device 106 includes, for example, an imaging member 120 and a cylindrical member 122 having substantially a cylindrical shape, and the imaging member 120 is provided in the cylindrical member 122. For example, a cover glass (not illustrated) is provided at the aperture surface on the lower end (the lower edge in FIG. 2A and FIG. 2B) of the cylindrical member 122 to protect the imaging member 120.

For example, a light source (not illustrated) is provided inside the cylindrical member 122 so that, during the imaging, the light source emits illumination light toward the object through the cover glass. The reflected light (observation light) from the object, which has been irradiated with the illumination light, enters the imaging member 120 through the cover glass (not illustrated) so that the imaging member 120 obtains the image signal representing the object (the image signal representing a medical-use captured image). As the imaging member 120, the configuration used in various known electronic microscopes may be applied.

For example, the imaging member 120 includes an optical system 120a and an image sensor 120b including an imaging element to capture the image of the observation target with the light passing through the optical system 120a. The optical system 120a includes, for example, optical elements such as one or more lenses, e.g., an objective lens, a zoom lens, or a focus lens, and a mirror. Examples of the image sensor 120b include an image sensor such as a complementary metal oxide semiconductor (CMOS) or a charge coupled device (CCD) using a plurality of imaging elements.

For example, the imaging member 120 includes two or more imaging devices including the optical system 120a and the image sensor 120b to function as what is called a stereo camera. In the configuration of the imaging device 106 functioning as a stereo camera, the optical system may be a Galilean optical system or a Greenough optical system. The imaging device included in the imaging member 120 has one or more functions that are typically provided in an electronic microscope, e.g., the zoom function (the optical zoom function or the electronic zoom function or both) or the auto focus (AF) function.

The imaging member 120 may be configured to enable high-resolution imaging such as what is called 4K or 8K. As the imaging member 120 is configured to enable the high-resolution imaging, images may be displayed on the display device 200 including the large display screen of, for example, 50 or more inches while a predetermined resolution (e.g., Full HD image quality) is maintained, whereby the visibility of the operator who views the display screen is improved. Furthermore, as the imaging member 120 is configured to enable the high-resolution imaging, a predetermined resolution may be maintained even when an enlarged captured image is displayed on the display screen of the display device 200 due to the electronic zoom function. Moreover, when a predetermined resolution is maintained by using an electronic zoom function, the performance of the imaging device 106 for the optical zoom function may be reduced, which results in a simpler optical system of the imaging device 106 and a smaller size of the imaging device 106.

The imaging device 106 is provided with, for example, various operating devices to control the operation of the imaging device 106. For example, in FIG. 2A and FIG. 2B, the imaging device 106 is provided with a zoom switch 124, a focus switch 126, and an operation-mode changeover switch 128. It is obvious that the positions and the shapes of the zoom switch 124, the focus switch 126, and the operation-mode changeover switch 128 are not limited to the example illustrated in FIG. 2A and FIG. 2B.

The zoom switch 124 and the focus switch 126 are examples of the operating device that adjusts the imaging condition of the imaging device 106. The zoom switch 124 includes, for example, a zoom-in switch 124a that increases the zoom magnification (magnifying power) and a zoom-out switch 124b that decreases the zoom magnification. The zoom switch 124 is operated to adjust the zoom magnification so that the zoom is adjusted.

The focus switch 126 includes, for example, a long-distance focus switch 126a that increases the focal length to the observation target (object) and a short-distance focus switch 126b that decreases the focal length to the observation target. The focus switch 126 is operated to adjust the focal length so that the focus is adjusted.

The operation-mode changeover switch 128 is an example of the operating device that changes the operation mode of the arm 104 in the imaging device 106. The operation-mode changeover switch 128 is operated to change the operation mode of the arm 104. Examples of the operation mode of the arm 104 include the fixed mode and the free mode, as described above.

Examples of an operation on the operation-mode changeover switch 128 include the operation to press the operation-mode changeover switch 128. For example, the operation mode of the arm 104 is the free mode when the operator is pressing the operation-mode changeover switch 128, and the operation mode of the arm 104 is the fixed mode when the operator is not pressing the operation-mode changeover switch 128.

The imaging device 106 is provided with, for example, a slip-proof member 130 and a projection member 132 to further improve the operability and the user-friendliness in operation for the operator who performs operation on the various operating devices.

The slip-proof member 130 is a member provided to prevent the slippage of an operating body, such as hand, when, for example, the operator operates the cylindrical member 122 with the operating body. The slip-proof member 130 is formed of, for example, a material having a high coefficient of friction and is configured to have a recess and a protrusion so as to prevent the slippage.

The projection member 132 is a member provided to, for example, prevent the operating body, such as the hand, from blocking the field of view of the optical system 120a when the operator operates the cylindrical member 122 with the operating body or to prevent the cover glass (not illustrated) from getting dirty due to the contact between the cover glass and the operating body when the operator operates the cylindrical member 122 with the operating body.

It is obvious that the installation positions and the shapes of the slip-proof member 130 and the projection member 132 are not limited to the example illustrated in FIG. 2A and FIG. 2B. The imaging device 106 may omit the slip-proof member 130 or the projection member 132 or both.

An image signal (image data) generated during the imaging of the imaging device 106 is subjected to image processing by, for example, the processor functioning as the control unit described later. The image processing according to the present embodiment is, for example, one or more processes among various types of processes such as gamma correction, white balance adjustment, image enlargement or reduction due to the electronic zoom function, and inter-pixel correction. The image processing according to the present embodiment may include for example the image processing described later.

When the medical observation system according to the present embodiment includes a control device (not illustrated) that controls various operations of the medical observation device 100, the control device (not illustrated) may perform the image processing according to the present embodiment. In this case, the control device (not illustrated) functions as an image processing apparatus that is capable of performing the image processing according to the present embodiment.

The medical observation device 100 transmits, for example, a display control signal and an image signal having undergone the above-described image processing to the display device 200. After the display control signal and the image signal are transmitted to the display device 200, the display screen of the display device 200 displays the medical-use captured image that captures the observation target (e.g., the captured image that captures the surgery site) as being enlarged or reduced at a desired magnification by using the optical zoom function or the electronic zoom function or both.

The medical observation device 100 illustrated in FIG. 1 includes, for example, the hardware configuration described with reference to FIGS. 1 and 2. The hardware configuration of the medical observation device according to the present embodiment is not limited to the configuration described with reference to FIGS. 1 and 2. For example, the medical observation device according to the present embodiment may omit the base 102 and may be configured such that the arm 104 is directly attached to the ceiling, the wall surface, or the like, of the operation room. For example, when the arm 104 is attached to the ceiling, the medical observation device according to the present embodiment is configured such that the arm 104 hangs from the ceiling.

Although the arm 104 is configured to enable six degrees of freedom with regard to the driving of the imaging device 106 in the example illustrated in FIG. 1, the configuration of the arm 104 is not limited to the configuration enabling six degrees of freedom with regard to the driving of the imaging device 106. For example, the arm 104 may be configured such that the imaging device 106 is movable as appropriate depending on a use application, and the number and the arrangement of joint parts and links, the direction of the drive shaft of a joint part, and the like, may be set as appropriate so as to have the desired degree of freedom of the arm 104.

Although the imaging device 106 is provided with various operating devices for controlling the operation of the imaging device 106 in the example illustrated in FIGS. 1 and 2, the imaging device 106 may omit all or a part of the operating devices illustrated in FIGS. 1 and 2. For example, another part included in the medical observation device according to the present embodiment other than the imaging device 106 may be provided with various operating devices for controlling the operation of the imaging device 106. As another example, various operating devices for controlling the operation of the imaging device 106 may be an external operating device, such as a foot switch or a remote controller.

The imaging device 106 may be configured to enable the switching among multiple observation modes. Examples of the observation mode according to the present embodiment include the observation mode for imaging with natural light, the observation mode for imaging with special light, and the observation mode for imaging using an image enhancement observation technique such as the narrow band imaging (NBI). The special light according to the present embodiment is, for example, light in a specific wavelength band, such as light in a near-infrared wavelength band or light in a fluorescence wavelength band for fluorescent observation using 5-aminolevulinic acid (5-ALA).

An example of the configuration of the imaging device 106 enabling the switching among multiple observation modes includes "the configuration including: a filter that permits the transmission of light in a specific wavelength band and does not allow the transmission of light in other wavelength bands; and a moving system that selectively locates the filter on the optical path". Examples of the specific wavelength band transmitted through the filter according to the present embodiment include a near-infrared wavelength band (e.g., a wavelength band from approximately 0.7 micrometers to approximately 2.5 micrometers), a fluorescence wavelength band for fluorescent observation using 5-ALA (e.g., a wavelength band from approximately 0.6 micrometers to approximately 0.65 micrometers), or an indocyanine green (ICG) fluorescence wavelength band (e.g., a wavelength band from approximately 0.82 micrometers to approximately 0.85 micrometers).

The imaging device 106 may be provided with multiple filters having different wavelength bands for transmission. In the case described above, the filter provided on the optical path allows the imaging with light in a specific wavelength band; however, it is obvious that the configuration of the imaging device 106 for the imaging with light in a specific wavelength band is not limited to the above-described example.

1-2. An Observation System According to a Second Example

The observation system according to the first example is described above. The medical observation system 1000 according to the embodiment is not limited to the configuration according to the first example illustrated in FIG. 1. Next, as a second example of an observation system, an example where the observation system is the medical observation system 1000 including the medical observation device 100 functioning as an endoscope device is described.

FIG. 3 is a diagram that illustrates a second example of the external configuration of the medical observation system 1000 according to the embodiment. The medical observation system 1000 illustrated in FIG. 3 includes, for example, the medical observation device 100 and the display device 200. For example, when the medical observation device 100 illustrated in FIG. 3 is used during a surgery, the operator observes the surgery site while viewing the medical-use captured image that is captured by the medical observation device 100 and displayed on the display screen of the display device 200 and gives various treatments, such as the procedure corresponding to a surgical method, on the surgery site.

The medical observation system 1000 according to the second example is not limited to the example illustrated in FIG. 3. For example, as is the case with the medical observation system 1000 according to the first example, the medical observation system 1000 according to the second example may further include a control device (not illustrated) that controls various operations of the medical observation device 100. Furthermore, as is the case with the medical observation system 1000 according to the first example, the medical observation system 1000 according to the second example may include the medical observation devices 100 or the display devices 200 or both.

(1) The Display Device 200

The display device 200 is a display unit of the medical observation system 1000 according to the second example, and the display device 200 corresponds to an external display device for the medical observation device 100. The display device 200 included in the medical observation system 1000 according to the second example is the same as the display device 200 included in the medical observation system 1000 according to the first example.

(2) the Medical Observation Device 100

The medical observation device 100 illustrated in FIG. 3 includes, for example, an insertion member 134, a light source unit 136, a light guide 138, a camera head 140, a cable 142, and a control unit 144. The medical observation device 100 is driven with, for example, the electric power supplied from an internal power source, such as a battery, included in the medical observation device 100 or the electric power supplied from an externally connected power source.

The insertion member 134 has an elongated shape and includes an internal optical system that focuses the incident light. The distal end of the insertion member 134 is inserted into, for example, the body cavity of the patient. The rear end of the insertion member 134 is removably coupled to the distal end of the camera head 140. The insertion member 134 is coupled to the light source unit 136 via the light guide 138 so that the light is supplied from the light source unit 136. The insertion member 134 may be formed of, for example, a material having no flexibility or may be formed of a material having flexibility. The medical observation device 100 may be called as a rigid endoscope or a flexible endoscope depending on the material of the insertion member 134.

The light source unit 136 is coupled to the insertion member 134 via the light guide 138. The light source unit 136 supplies light to the insertion member 134 via the light guide 138.

The light source unit 136 includes, for example, a plurality of light sources that emit light having a different wavelength. Examples of the light sources included in the light source unit 136 include a light source that emits red light, a light source that emits green light, and a light source that emits blue light. Examples of the light source that emits red light include one or more red light emitting diodes. Examples of the light source that emits green light include one or more green light emitting diodes. Examples of the light source that emits blue light include one or more blue light emitting diodes. It is obvious that the light sources included in the light source unit 136 are not limited to the example described above. For example, the light source unit 136 includes the light sources on a single chip or includes the light sources on multiple chips. The light source unit 136 is coupled to the control unit 144 via a wired line or wirelessly, and the emission of the light source unit 136 is controlled by the control unit 144.

The light supplied from the insertion member 134 is output from the distal end of the insertion member 134 and is emitted toward the observation target, such as tissue, inside the body cavity of the patient. Then, the reflected light from the observation target is focused by the optical system inside the insertion member 134.

The camera head 140 is a device that captures the imaging target. For example, the camera head 140 captures the observation target. The camera head 140 is coupled to the control unit 144 via the cable 142 that is a signal transmission member.

The camera head 140 includes an image sensor to execute the photoelectric conversion on the reflected light entering from the observation target and focused by the insertion member 134 so as to capture the observation target and output the image signal (the signal representing the medical-use captured image) obtained during the imaging to the control unit 144 via the cable 142. Examples of the image sensor included in the camera head 140 include an image sensor using a plurality of imaging elements, such as a CMOS or a CCD.

In the medical observation device 100 functioning as an endoscope device, for example, the insertion member 134, the light source unit 136, and the camera head 140 function as "the imaging device inserted into the inside of the body of the patient to capture the inside of the body".

The medical observation device 100 functioning as an endoscope device may include a plurality of imaging devices to function as, for example, what is called a stereo camera. In the configuration of the imaging device functioning as a stereo camera, the optical system may be a Galilean optical system or a Greenough optical system as is the case with the medical observation device 100 included in the medical observation system 1000 according to the first example.

The control unit 144 controls the imaging device. More specifically, the control unit 144 controls the light source unit 136 and the camera head 140. The control unit 144 includes a communication device (not illustrated) to transmit an image signal output from the camera head 140 to the display device 200 via any wireless communication or any wired communication. The control unit 144 may transmit an image signal and a display control signal to the display device 200.

Examples of the communication device (not illustrated) included in the control unit 144 include an IEEE 802.15.1 port and a transmission/reception circuitry (wireless communication), an IEEE 802.11 port and a transmission/reception circuitry (wireless communication), a communication antenna and an RF circuitry (wireless communication), an optical communication device (wired communication or wireless communication), or a LAN terminal and a transmission/reception circuitry (wired communication). The communication device (not illustrated) may be configured to perform communications with one or more external devices by using multiple communication methods.

The control unit 144 may perform a predetermined process on an image signal output from the camera head 140 and transmit the image signal having undergone the predetermined process to the display device 200. Examples of the predetermined process on an image signal include white balance adjustment, image enlargement or reduction in accordance with the electronic zoom function, and inter-pixel correction. The predetermined process on an image signal may include, for example, the image processing described later.

The control unit 144 may store a medical-use captured image based on an image signal. Examples of the control unit 144 include a camera control unit (CCU).

The medical observation device 100 functioning as an endoscope device includes the hardware configuration described with reference to, for example, FIG. 3. In the medical observation device 100 functioning as an endoscope device, for example, the insertion member 134, the light source unit 136, and the camera head 140 function as the imaging device, and the control unit 144 controls the imaging of the imaging device.

1-3. The Observation System According to Another Example

The observation system according to the embodiment is not limited to the configuration according to the first example illustrated in FIG. 1 and the configuration according to the second example illustrated in FIG. 3. For example, the medical observation device 100 included in the medical observation system 1000 according to the embodiment may be configured such that the optical medical observation device 100 is provided with a plurality of imaging devices. The image processing described later may be applied to the optical medical observation device 100 provided with the imaging devices. In the example described below, the medical observation device 100 included in the medical observation system 1000 according to the embodiment is the medical observation device 100 illustrated in FIGS. 1 and 3. The observation system and the observation device according to the embodiment are not limited to the medical purpose.

Figure 4:
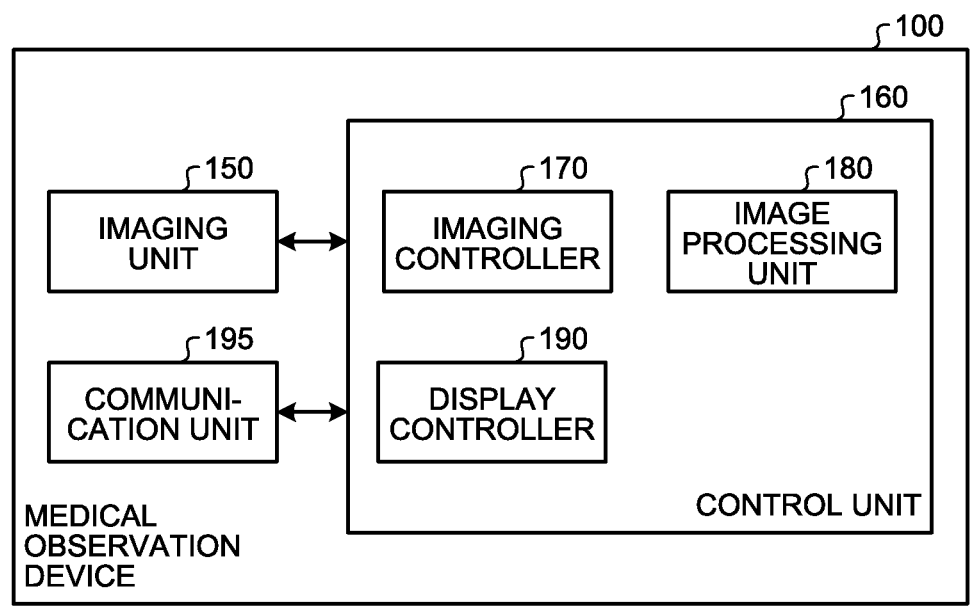
FIG. 4 is a block diagram that illustrates an example of the functional configuration of the medical observation device according to the embodiment.

2. Functional Configuration of the Observation Device According to the Embodiment The external configuration of the observation system according to the embodiment is described above. Next, a functional configuration of the medical observation device 100 according to the embodiment is described. FIG. 4 is a block diagram that illustrates an example of the functional configuration of the medical observation device 100 according to the embodiment. As illustrated in FIG. 4, the medical observation device 100 includes, for example, an imaging unit 150, a control unit 160, and a communication unit 195.

(1) The Imaging Unit 150

The imaging unit 150 has the function to capture the imaging target. For example, the imaging unit 150 captures the observation target as an imaging target. The imaging unit 150 includes, for example, "the imaging device 106" (in the case of the medical observation device 100 illustrated in FIG. 1) and "the insertion member 134, the light source unit 136, and the camera head 140" (in the case of the medical observation device 100 illustrated in FIG. 3). The imaging of the imaging unit 150 is controlled by, for example, the control unit 160. A signal generated when the imaging unit 150 captures the observation target is hereinafter also referred to as an imaging signal (first signal). An imaging signal generated by the imaging unit 150 is input to the control unit 160.

The imaging signal includes an RGB signal that is a signal corresponding to multiple wavelength bands. Examples of the wavelength bands include at least a red wavelength band, a green wavelength band, and a blue wavelength band. The red wavelength band corresponds to an R component of an RGB signal. A green wavelength band corresponds to a G component of an RGB signal. A blue wavelength band corresponds to a B component of an RGB signal.

(2) The Control Unit 160

The control unit 160 is an image processing apparatus that controls the overall operation of the observation device. According to the embodiment, as the control unit 160 is included in the medical observation device 100, the control unit 160 may function as a medical image processing apparatus. The control unit 160 includes, for example, the above-described processor (not illustrated) to provide the function to control the overall medical observation device 100. The control unit 160 takes a lead role in performing a process regarding the image processing described later. The process regarding the image processing by the control unit 160 may be separately performed by a plurality of processing circuitries (e.g., a plurality of processors). As illustrated in FIG. 4, the control unit 160 includes, for example, an imaging controller 170, the image processing unit 180, and a display controller 190.

(2-1) The Imaging Controller 170

The imaging controller 170 controls an imaging device included in the imaging unit 150. The control on the imaging device may be, for example, the control on one or more functions typically provided in an electronic microscope, e.g., the control on the AF function including at least the zoom function (the optical zoom function and the electronic zoom function).

(2-2) The Image Processing Unit 180

The image processing unit 180 performs the image processing according to the present embodiment on multiple medical-use captured images obtained when the imaging devices capture the observation target. For example, the image processing unit 180 executes white balance adjustment on an imaging signal input from the imaging unit 150 and corresponding to multiple wavelength bands. According to the embodiment, it is assumed that the signal output after the white balance adjustment on an imaging signal includes the area having saturation. The signal including the area having saturation caused by the white balance adjustment is hereinafter also referred to as a saturation signal (second signal).

The image processing unit 180 performs the process to generate a luminance signal from a saturation signal. For example, the image processing unit 180 performs the conversion process to convert an RGB signal included in a saturation signal into a luminance signal so as to generate a luminance signal. The luminance signal is hereinafter also referred to as a Y signal. The luminance signal includes the area having saturation, as is the case with a saturation signal.

The image processing unit 180 performs the process to extract a detail component based on an imaging signal. The detail component is information indicating, for example, the detail of the surface of the imaging target. For example, the image processing unit 180 performs the process to directly extract a detail component from an imaging signal. The source from which a detail component is extracted is not limited to an imaging signal as long as the signal does not include the area having saturation.

The image processing unit 180 applies the extracted detail component to a luminance signal to generate a corrected luminance signal. As described above, the image processing unit 180 applies the detail component including the information on the imaging target before saturation occurs to the luminance signal including the area having saturation. Thus, the image processing unit 180 may restore the detail of the area having saturation.

The image processing unit 180 further performs the process to generate a color-difference signal from a saturation signal. For example, the image processing unit 180 performs the conversion process to convert an RGB signal included in a saturation signal into a color-difference signal so as to generate a color-difference signal. The image processing unit 180 generates an image based on the generated corrected luminance signal and color-difference signal.

(2-3) The Display Controller 190

For example, the display controller 190 transmits a display control signal and an image signal to the communication device (not illustrated) included in the communication unit 195 and causes the display control signal and the image signal to be transmitted to the display device 200 so as to control the display on the display device 200. An image signal transmitted by the display controller 190 may include an image signal having undergone the image processing by the image processing unit 180. The control on the communication by the communication unit 195 may be performed by the communication unit (not illustrated) included in the control unit 160.

The control unit 160 includes, for example, the image processing unit 180 to take a lead role in performing the image processing according to the present embodiment. The control unit 160 includes, for example, the imaging controller 170 and the display controller 190 to provide the function to control the overall medical observation device 100.

The functional configuration of the control unit 160 is not limited to the example illustrated in FIG. 4. For example, the control unit 160 may have any configuration in accordance with the separation of the functions of the medical observation device 100, e.g., the configuration in accordance with the separation of the image processing according to the present embodiment.

For example, when the medical observation device 100 has the configuration illustrated in FIG. 1, the control unit 160 may further include an arm controller (not illustrated) that controls the driving of the arm 104. An example of the control on the driving of the arm 104 may be "the application of a control signal for controlling the driving to an actuator (not illustrated) corresponding to each of the joint parts 110a, 110b, 110c, 110d, 110e, and 110f".

The medical observation device 100 uses, for example, the functional configuration illustrated in FIG. 4 to perform the image processing according to the present embodiment described later. The functional configuration of the medical observation device 100 according to the embodiment is not limited to the configuration illustrated in FIG. 4. For example, in the medical observation device 100 according to the embodiment, all or a part of the imaging controller 170, the image processing unit 180, and the display controller 190 illustrated in FIG. 4 may be provided separately (e.g., implemented by a different processing circuitry) from the control unit 160.

In the medical observation device 100 according to the embodiment, the functional configuration enabling the execution of the image processing according to the embodiment is not limited to the configuration illustrated in FIG. 4. For example, the medical observation device 100 according to the embodiment may have the functional configuration corresponding to the separation of the image processing according to the embodiment.

When the medical observation device 100 according to the embodiment includes the configuration illustrated in FIG. 1, the medical observation device 100 according to the embodiment includes an arm unit (not illustrated) including the arm 104. The arm 104 included in the arm unit (not illustrated) supports the imaging device 106 included in the imaging unit 150.

For example, it is assumed that the medical observation system 1000 according to the embodiment includes a control device (not illustrated) and the medical observation device 100 according to the embodiment is controlled by the control device (not illustrated). In this case, the medical observation device 100 according to the embodiment may omit the control unit 160.

The control device (not illustrated) includes a control unit having the same function and configuration as those of, for example, the control unit 160 to perform the image processing according to the embodiment described later. The control device (not illustrated) controls the operation of each component such as the imaging unit 150 included in the medical observation device 100 according to the embodiment. The control device (not illustrated) performs communications with the medical observation device 100 according to the embodiment via an included communication device or an externally coupled communication device to control the operation of each component included in the medical observation device 100 according to the embodiment.

Furthermore, it is assumed that, for example, the medical observation system 1000 according to the embodiment includes the control device (not illustrated), and the medical observation device 100 according to the embodiment is controlled by the control device (not illustrated). In this case, the medical observation device 100 according to the embodiment may be configured such that a part of the functions of the control unit 160 is not provided.

(3) The Communication Unit 195

The communication unit 195 is a communication unit included in the medical observation device 100 to provide the function to communicate with an external device, such as the display device 200, wirelessly or via a wired line. The communication unit 195 includes, for example, the above-described communication device (not illustrated). The communication of the communication unit 195 is controlled by, for example, the control unit 160.

For example, the medical observation device 100 according to the embodiment may omit the communication unit 195 when the communication is established with an external device via an external communication device having the same function and configuration as those of the communication unit 195.

Summary of a Problem

With reference to FIG. 5, the summary of a problem is given here. FIG. 5 is a diagram that illustrates an example of the image processing. The upper section of FIG. 5 illustrates an example where, when the white balance adjustment is executed on an imaging signal, the signal level of each component of the RGB signal after the adjustment has the same value. The lower section of FIG. 5 illustrates an example where, when the white balance adjustment is executed on an imaging signal, saturation occurs in only the R component of the RGB signal after the adjustment. FIG. 5 illustrates an example where saturation occurs when the signal level is more than 100% and saturation does not occur when the signal level is equal to or less than 100%. In the upper section of FIG. 5, the signal level of each component of the RGB signal is adjusted to be 80% due to the white balance adjustment. The signal level may be adjusted to any value, such as 100%, 50%, or 30%, due to the white balance adjustment if the signal level of each component of the RGB signal is the same value (the same percentage) after the adjustment.

When the white balance adjustment is performed on an RGB signal, the gain is typically applied to each component such that the signal level of each component has the same value. For example, in the example illustrated in the upper section of FIG. 5, as the signal level of a G component 62a is 80%, the gain is applied to an R component 61a and a B component 63a such that the signal levels of the R component 61a and the B component 63a become 80%. Then, when the RGB signal including an R component 61b, a G component 62b, and a B component 63b with the signal level of 80% is converted into a Y signal, a Y signal 64a with the signal level of 80% is obtained. When an image is generated based on the Y signal 64a, no saturation occurs and no detail is lost in the generated image.

Conversely, it is assumed that, in the input RGB signal, the signal level of an R component 61c is highest and the signal levels of a G component 62c and a B component 63c are lower than the signal level of the R component 61c, as illustrated in the lower section of FIG. 5. When the same gain as that in the upper section of FIG. 5 is applied during the white balance adjustment on each component of the RGB signal, the signal level of an R component 61d exceeds 100%. As an R component 65, which is the part that exceeds 100%, is cut, saturation occurs. The signal levels of the G component 62c and the B component 63c are lower than the signal level of the R component 61c. Although the signal level of a B component 63d, to which the same gain as that in the upper section of FIG. 5 is applied, is amplified as compared to the signal level before the gain is applied, the amplification percentage of the signal level of the B component 63d is lower than that of the signal level of the R component 61d and is less than 100%. The signal level of a G component 62d is not changed after the same gain as that in the upper section of FIG. 5 is applied. When the RGB signal including the R component 61d with the signal level of 100% and the G component 62d and the B component 63d with the signal level of less than 100% is converted into a Y signal, a Y signal 64b with the signal level of less than 100% is obtained. When an image is generated based on the Y signal 64b, the detail is lost from the generated image due to the occurrence of saturation.

The embodiment has been developed with a focus on the above-described point, and it discloses the technique that makes it possible to restore the detail of the area having saturation. Each embodiment is sequentially described below in detail. In the following embodiment described below, it is assumed that saturation occurs when the signal level is more than 100% and no saturation occurs when the signal level is equal to or less than 100%. The value as the criterion for determining whether saturation has occurred is not limited to 100% and may be any value.

3. The Image Processing Unit According to a First Embodiment

Figure 6:
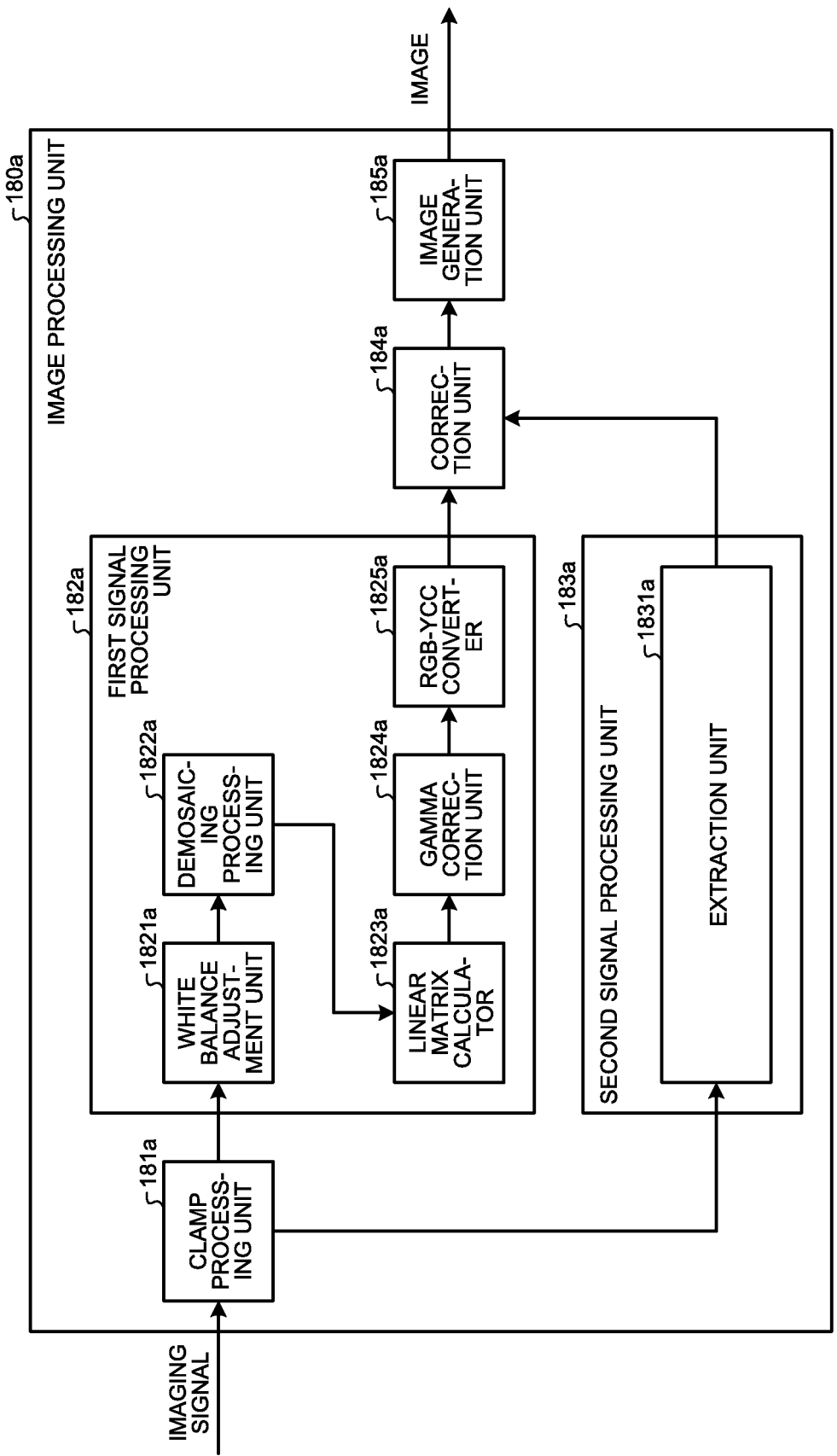
FIG. 6 is a block diagram that illustrates an example of the functional configuration of an image processing unit according to a first embodiment.

First, the image processing unit according to a first embodiment is described. FIG. 6 is a block diagram that illustrates an example of the functional configuration of the image processing unit 180a according to the first embodiment. In the example described in the first embodiment, a correction unit 184a applies a detail component to the entire luminance signal output from a first signal processing unit 182a.

3-1. Functional Configuration of the Image Processing Unit

As illustrated in FIG. 6, the image processing unit 180a includes a clamp processing unit 181a, the first signal processing unit 182a, a second signal processing unit 183a, the correction unit 184a, and an image generation unit 185a.

(1) The Clamp Processing Unit 181a

The clamp processing unit 181a has the function to perform a clamp process on an input signal. For example, the clamp processing unit 181a performs a clamp process on an imaging signal input from the imaging unit 150. The clamp processing unit 181a outputs an imaging signal having undergone a clamp process to the first signal processing unit 182a and the second signal processing unit 183a.

(2) The First Signal Processing Unit 182a

The first signal processing unit 182a has the function to execute the white balance adjustment on an input signal to generate a luminance signal from the signal having undergone the white balance adjustment. For example, the first signal processing unit 182a generates a luminance signal from an imaging signal input from the clamp processing unit 181a. Specifically, first, the first signal processing unit 182a executes the white balance adjustment on an imaging signal input from the clamp processing unit 181a. Then, the first signal processing unit 182a generates a luminance signal from a saturation signal generated due to the white balance adjustment.

The first signal processing unit 182a has the function to generate a color-difference signal from the signal having undergone the white balance adjustment. For example, the first signal processing unit 182a further generates a color-difference signal from a saturation signal.

To implement the above-described function, the first signal processing unit 182a includes a white balance adjustment unit 1821a, a demosaicing processing unit 1822a, a linear matrix calculator 1823a, a gamma correction unit 1824a, and an RGB-YCC converter 1825a, as illustrated in FIG. 6.

(2-1) The White Balance Adjustment Unit 1821a

The white balance adjustment unit 1821a has the function to conduct the white balance adjustment on an input signal. For example, the white balance adjustment unit 1821a executes the white balance adjustment on an imaging signal input from the clamp processing unit 181a. The white balance adjustment unit 1821a outputs a saturation signal output after the white balance adjustment to the demosaicing processing unit 1822a.

(2-2) The Demosaicing Processing Unit 1822a

The demosaicing processing unit 1822a has the function to perform a demosaicing process on an input signal. For example, the demosaicing processing unit 1822a performs a demosaicing process on a saturation signal input from the white balance adjustment unit 1821a. The demosaicing processing unit 1822a outputs the saturation signal having undergone the demosaicing process to the linear matrix calculator 1823a.

(2-3) The Linear Matrix Calculator 1823a

The linear matrix calculator 1823a has the function to perform a linear matrix calculation on an input signal. For example, the linear matrix calculator 1823a performs a linear matrix calculation on a second imaging signal input from the demosaicing processing unit 1822a. The linear matrix calculator 1823a outputs the saturation signal having undergone the linear matrix calculation to the gamma correction unit 1824a.

(2-4) The Gamma Correction Unit 1824a

The gamma correction unit 1824a has the function to perform a gamma correction on an input signal. For example, the gamma correction unit 1824a performs a gamma correction on a saturation signal input from the linear matrix calculator 1823a. The gamma correction unit 1824a outputs the saturation signal having undergone the gamma correction to the RGB-YCC converter 1825a.

(2-5) The RGB-YCC Converter 1825a

The RGB-YCC converter 1825a has the function to generate a luminance signal from an input signal. For example, the RGB-YCC converter 1825a performs a conversion process to convert an RGB signal included in a saturation signal input from the gamma correction unit 1824a into a luminance signal. The RGB-YCC converter 1825a outputs the luminance signal generated during the conversion process to the correction unit 184a.

The RGB-YCC converter 1825a has the function to generate a color-difference signal from an input signal. For example, the RGB-YCC converter 1825a performs the conversion process to convert an RGB signal included in a saturation signal input from the gamma correction unit 1824a into a color-difference signal. The RGB-YCC converter 1825a outputs the color-difference signal generated during the conversion process to the correction unit 184a.

(3) The Second Signal Processing Unit 183a

The second signal processing unit 183a has the function to extract a detail component from an input signal. For example, the second signal processing unit 183a extracts a detail component based on an imaging signal input from the clamp processing unit 181a. To implement the function, the second signal processing unit 183a includes an extraction unit 1831a, as illustrated in FIG. 6.

(3-1) The Extraction Unit 1831a

The extraction unit 1831a has the function to extract a detail component from an input signal. For example, the extraction unit 1831a extracts a detail component from an imaging signal input from the clamp processing unit 181a. The extraction unit 1831a outputs the extracted detail component to the correction unit 184a.

There is no particular limitation on the method for the extraction unit 1831a to extract a detail component from an imaging signal. The extraction unit 1831a may use, for example, a high-pass filter (HPF) that cuts off low-frequency signals and allows the passage of only high-frequency signals. The extraction unit 1831a cuts off components (e.g., DC components) of less than a predetermined frequency with the high-pass filter to extract a detail component from an imaging signal. Here, the predetermined frequency is, for example, the upper limit value of the frequency of a DC component. Thus, the extraction unit 1831a may extract a detail component including no DC components from an imaging signal.

(4) The Correction Unit 184a

The correction unit 184a has the function to perform a correction process on an input signal. For example, with regard to a luminance signal, the correction unit 184a applies a detail component input from the extraction unit 1831a to a luminance signal input from the RGB-YCC converter 1825a to generate a corrected luminance signal. The corrected luminance signal is a luminance signal in which a detail component of the area having saturation has been restored. The correction unit 184a applies a detail component to a luminance signal so as to restore the detail of the area having saturation. The correction unit 184a outputs the corrected luminance signal, which is generated during the correction process, to the image generation unit 185a.

The correction unit 184a adds a detail component to a luminance signal at a predetermined ratio to generate a corrected luminance signal. The method for the correction unit 184a to apply a detail component to a luminance signal is not limited to the addition. For example, the correction unit 184a may subtract a detail component from a luminance signal at a predetermined ratio.

The correction unit 184a may adjust the signal level of the corrected luminance signal so as to be decreased. For example, the correction unit 184a may decrease the addition ratio for adding a detail component to a luminance signal so as to reduce the signal level of the corrected luminance signal. For example, the correction unit 184a may increase the subtraction ratio for subtracting a detail component from a luminance signal so as to reduce the signal level of the corrected luminance signal. For example, the correction unit 184a may multiply a corrected luminance signal, which is generated by adding or subtracting a detail component, by a predetermined coefficient to reduce the signal level of the corrected luminance signal as compared with the corrected luminance signal at the time of generation. When the signal level of a corrected luminance signal is adjusted to be reduced, it is preferable that the correction unit 184a adjusts the signal level of the corrected luminance signal in consideration of the amplification of the signal level at the side of the display device 200. For example, the correction unit 184a adjusts the signal level of the corrected luminance signal such that saturation would not occur in the displayed image even when the signal level is amplified by the display device 200. This allows the display device 200 to display the image in which, even when the signal level of the image signal is amplified, no saturation occurs and the detail has been restored.

(5) The Image Generation Unit 185a

The image generation unit 185a has the function to generate an image based on an input signal. For example, the image generation unit 185a generates an image based on a color-difference signal and a corrected luminance signal input from the correction unit 184a. The image generation unit 185a outputs the generated image as an image signal to the communication unit 195. The image generated by the image generation unit 185a is transmitted as an image signal to the display device 200 via the communication unit 195 and is displayed as an image on the display device 200.

3-2. Flow of Image Processing

Figure 7:
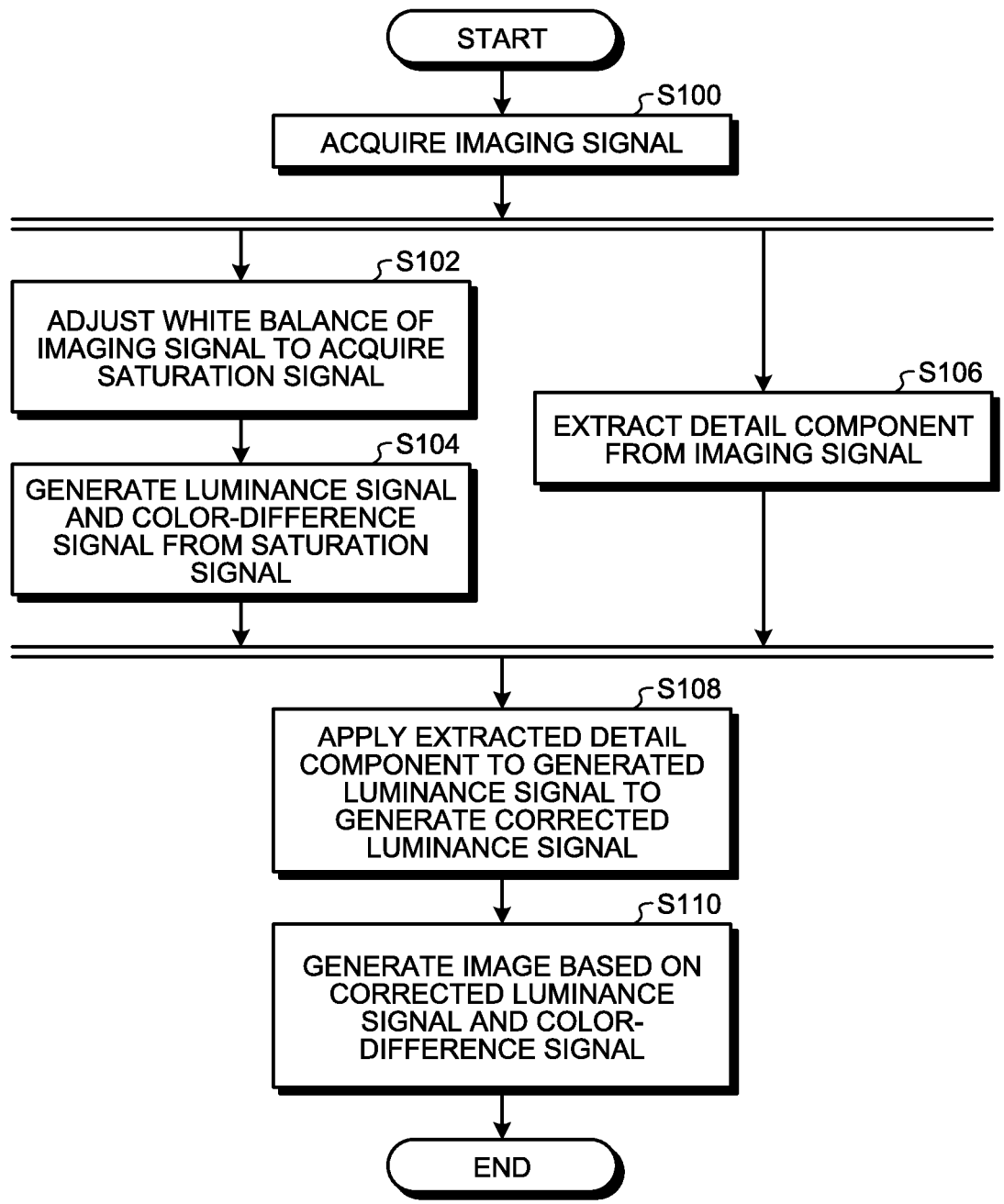
FIG. 7 is a flowchart that illustrates the flow of image processing according to the first embodiment.

FIG. 7 is a flowchart that illustrates the flow of image processing according to the first embodiment. First, the image processing unit 180a acquires an imaging signal (S100). Subsequently, the image processing unit 180a adjusts the white balance of the imaging signal to acquire a saturation signal (S102). Then, the image processing unit 180a generates a luminance signal and a color-difference signal from the acquired saturation signal (S104). In parallel with the operations at S102 and S104, the image processing unit 180a extracts a detail component from the imaging signal (S106).

The image processing unit 180a applies the extracted detail component to the generated luminance signal to generate a corrected luminance signal (S108). Then, the image processing unit 180a generates an image based on the generated corrected luminance signal and the color-difference signal (S110).

4. The Image Processing Unit According to the Second Embodiment

Figure 8:
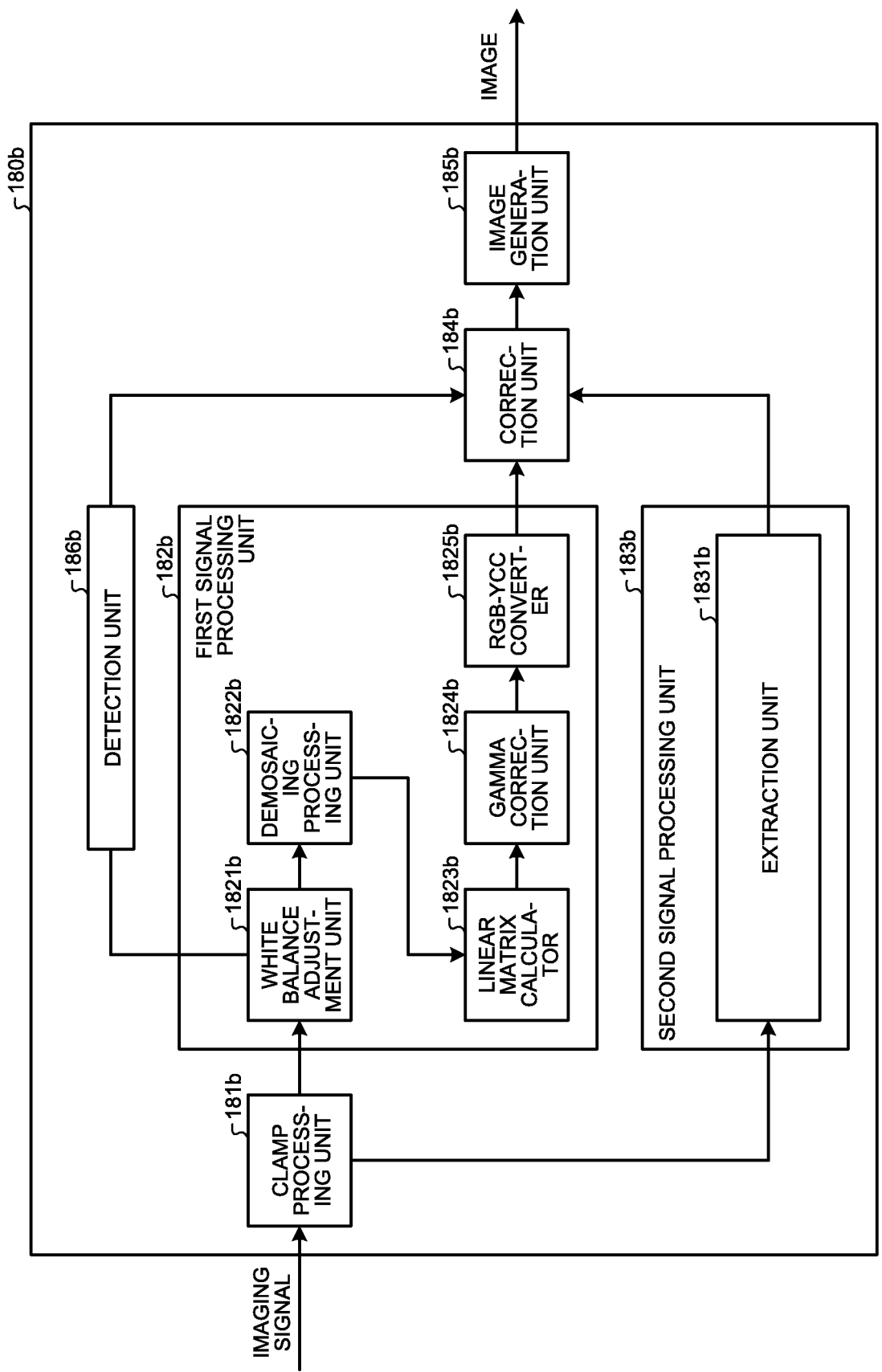
FIG. 8 is a block diagram that illustrates an example of the functional configuration of an image processing unit according to a second embodiment.

The image processing unit according to the first embodiment is described above. Next, the image processing unit according to the second embodiment is described. FIG. 8 is a block diagram that illustrates an example of the functional configuration of the image processing unit 180b according to the second embodiment. In the example described according to the first embodiment, the correction unit 184a applies a detail component to the entire luminance signal output from the first signal processing unit 182a. In the example described according to the second embodiment, a correction unit 184b applies a detail component only to the area having saturation. The part different from that in the first embodiment is described below in detail.

4-1. Functional Configuration of the Image Processing Unit

As illustrated in FIG. 8, the image processing unit 180b includes a clamp processing unit 181b, a first signal processing unit 182b, a second signal processing unit 183b, the correction unit 184b, an image generation unit 185b, and a detection unit 186b.

(1) The Clamp Processing Unit 181b

As the clamp processing unit 181b has the same function as that of the clamp processing unit 181a described in the first embodiment, the detailed description is omitted.

(2) The First Signal Processing Unit 182b

The first signal processing unit 182b has the same function as that of the first signal processing unit 182a described in the first embodiment. As illustrated in FIG. 8, the first signal processing unit 182b includes a white balance adjustment unit 1821b, a demosaicing processing unit 1822b, a linear matrix calculator 1823b, a gamma correction unit 1824b, and an RGB-YCC converter 1825b.

(2-1) The White Balance Adjustment Unit 1821b

As the white balance adjustment unit 1821b has the same function as that of the white balance adjustment unit 1821a described in the first embodiment, the detailed description is omitted. The white balance adjustment unit 1821b is different from the white balance adjustment unit 1821a according to the first embodiment in that a saturation signal is output to the detection unit 186b as well as the demosaicing processing unit 1822b.

(2-2) The Demosaicing Processing Unit 1822b

As the demosaicing processing unit 1822b has the same function as that of the demosaicing processing unit 1822a described in the first embodiment, the detailed description is omitted.

(2-3) The Linear Matrix Calculator 1823b

As the linear matrix calculator 1823b has the same function as that of the linear matrix calculator 1823a described in the first embodiment, the detailed description is omitted.

(2-4) The Gamma Correction Unit 1824b

As the gamma correction unit 1824b has the same function as that of the gamma correction unit 1824a described in the first embodiment, the detailed description is omitted.

(2-5) The RGB-YCC Converter 1825b

As the RGB-YCC converter 1825b has the same function as that of the RGB-YCC converter 1825a described in the first embodiment, the detailed description is omitted.

(3) The Second Signal Processing Unit 183b

The second signal processing unit 183b has the same function as that of the second signal processing unit 183a described in the first embodiment, the detailed description is omitted. The second signal processing unit 183b includes an extraction unit 1831b, as illustrated in FIG. 8.

(3-1) The Extraction Unit 1831b

As the extraction unit 1831b has the same function as that of the extraction unit 1831a described in the first embodiment, the detailed description is omitted.

(4) The Correction Unit 184b

Contrary to the correction unit 184a according to the first embodiment, the correction unit 184b has the function to perform a correction process on only the area having saturation and detected by the detection unit 186b. For example, the correction unit 184b applies only the detail component corresponding to the area having saturation and detected by the detection unit 186b to a luminance signal to generate a corrected luminance signal. Thus, as the correction unit 184b refrains from applying a detail component to the area where no saturation occurs, it is possible to prevent excessive enhancement at the area where no saturation occurs.

(5) The Image Generation Unit 185b

As the image generation unit 185b has the same function as that of the image generation unit 185a described in the first embodiment, the detailed description is omitted.

(6) The Detection Unit 186b

The detection unit 186b has the function to detect the area having saturation from an input signal. For example, the detection unit 186b detects the area having saturation from a saturation signal input from the white balance adjustment unit 1821b. The detection unit 186b outputs a detection result to the correction unit 184b. Thus, the correction unit 184b may determine the area to which a detail component is applied on the basis of a detection result of the detection unit 186b.

For example, the detection unit 186b detects the area having saturation on the basis of a threshold process on multiple wavelength bands corresponding to a saturation signal. Specifically, when the difference between the highest pixel value and the second highest pixel value among the pixel values corresponding to the respective wavelength bands is more than a predetermined threshold, the detection unit 186b detects the area corresponding to the wavelength bands as the area having saturation. For example, it is assumed that the pixel value of the R component of the RGB signal included in the saturation signal input to the detection unit 186b is the highest and the pixel value of the B component is the second highest. When the difference between the pixel value of the R component and the pixel value of the B component is more than the predetermined threshold, the detection unit 186b detects the area corresponding to the R component and the B component as the area having saturation. The method for the detection unit 186b to detect the area having saturation from a saturation signal is not limited to the above-described example.

The detection unit 186b detects at least one of the red wavelength band, the green wavelength band, and the blue wavelength band as the wavelength band in which saturation has occurred. The setting may be previously made such that the detection unit 186b detects a specific wavelength band as the wavelength band in which saturation has occurred. For example, the setting may be made such that the detection unit 186b detects the red wavelength band as the wavelength band in which the saturation has occurred. This allows the detection unit 186b to detect the area corresponding to the red wavelength band in which saturation has occurred as the area having saturation. That is, the detection unit 186b may detect the area having saturation from the areas presented in red on the image displayed on the display device 200.

The wavelength band in which saturation has occurred as detected by the detection unit 186b is not limited to only the red wavelength band. For example, the detection unit 186b may detect only the blue wavelength band as the wavelength band in which saturation has occurred. The detection unit 186b may detect only the green wavelength band as the wavelength band in which saturation has occurred. Furthermore, the detection unit 186b may detect any combination of the red wavelength band, the green wavelength band, and the blue wavelength band as the wavelength band in which saturation has occurred.

As a result detected by the detection unit 186b is output to the correction unit 184b, the correction unit 184b may restore the detail of the area having saturation among the areas displayed in red. Thus, restoring the detail of the area having saturation among the areas displayed in red is particularly effective for the medical observation device 100 whose imaging target is the inside of the body of a patient that is often in red.

The previously set specific wavelength band is not limited to the red wavelength band. For example, the previously set specific wavelength band may be only the green wavelength band or only the blue wavelength band. The specific wavelength band may be any combination of the red wavelength band, the green wavelength band, and the blue wavelength band.

4-2. Flow of Image Processing

Figure 9:
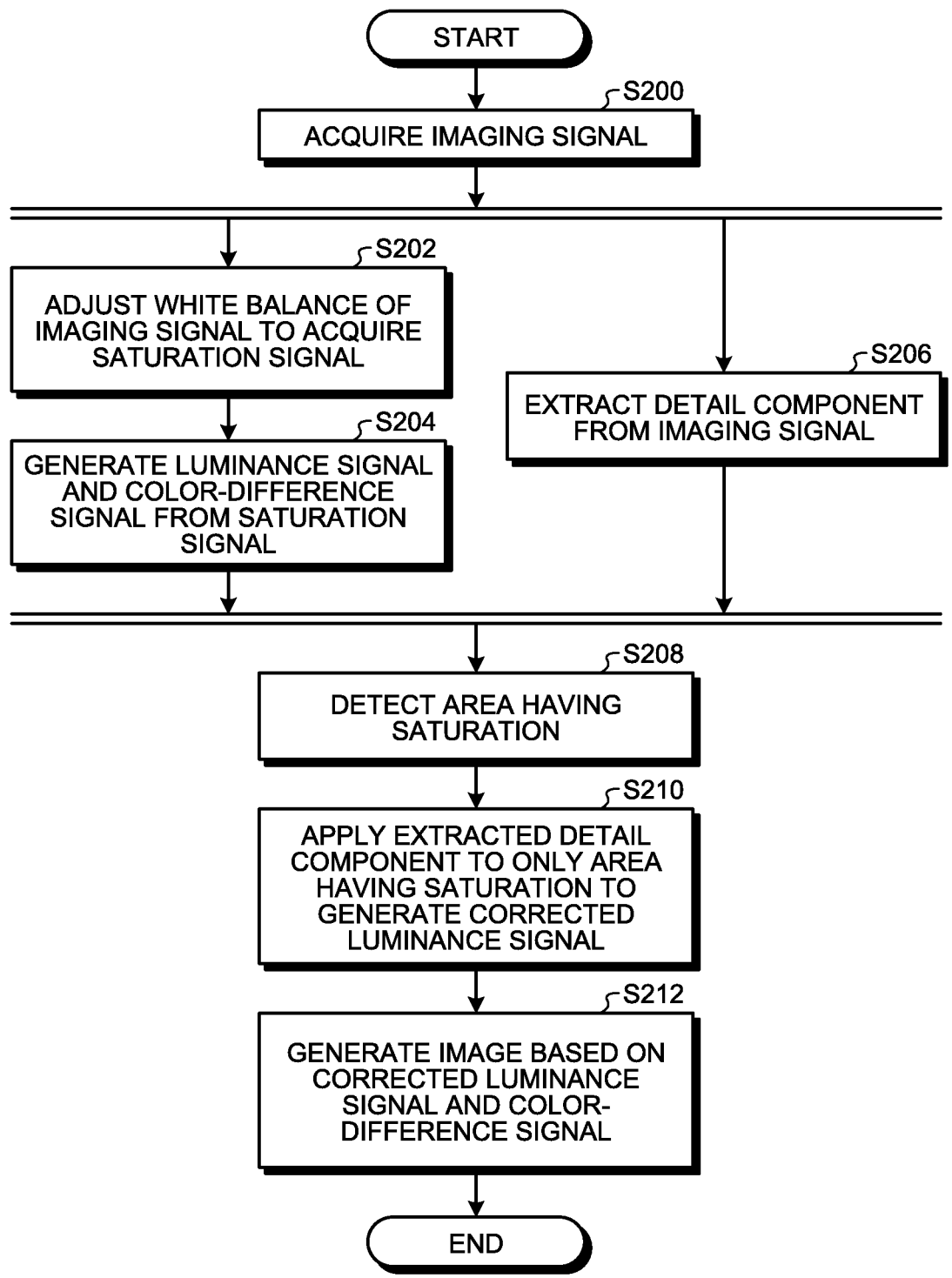
FIG. 9 is a flowchart that illustrates the flow of image processing according to the second embodiment.

FIG. 9 is a flowchart that illustrates the flow of image processing according to the second embodiment. First, the image processing unit 180b acquires an imaging signal (S200). Subsequently, the image processing unit 180b adjusts the white balance of an imaging signal to acquire a saturation signal (S202). Then, the image processing unit 180b generates a luminance signal and a color-difference signal from the acquired saturation signal (S204). In parallel with the operations at S202 and S204, the image processing unit 180b extracts a detail component from the imaging signal (S206).

The image processing unit 180b detects the area having saturation from the saturation signal (S208). Subsequently, the image processing unit 180b applies the extracted detail component to only the area having saturation in the luminance signal to generate a corrected luminance signal (S210). Then, the image processing unit 180b generates an image on the basis of the generated corrected luminance signal and the color-difference signal (S212).

5. An Image Processing Unit According to a Third Embodiment

Figure 10:
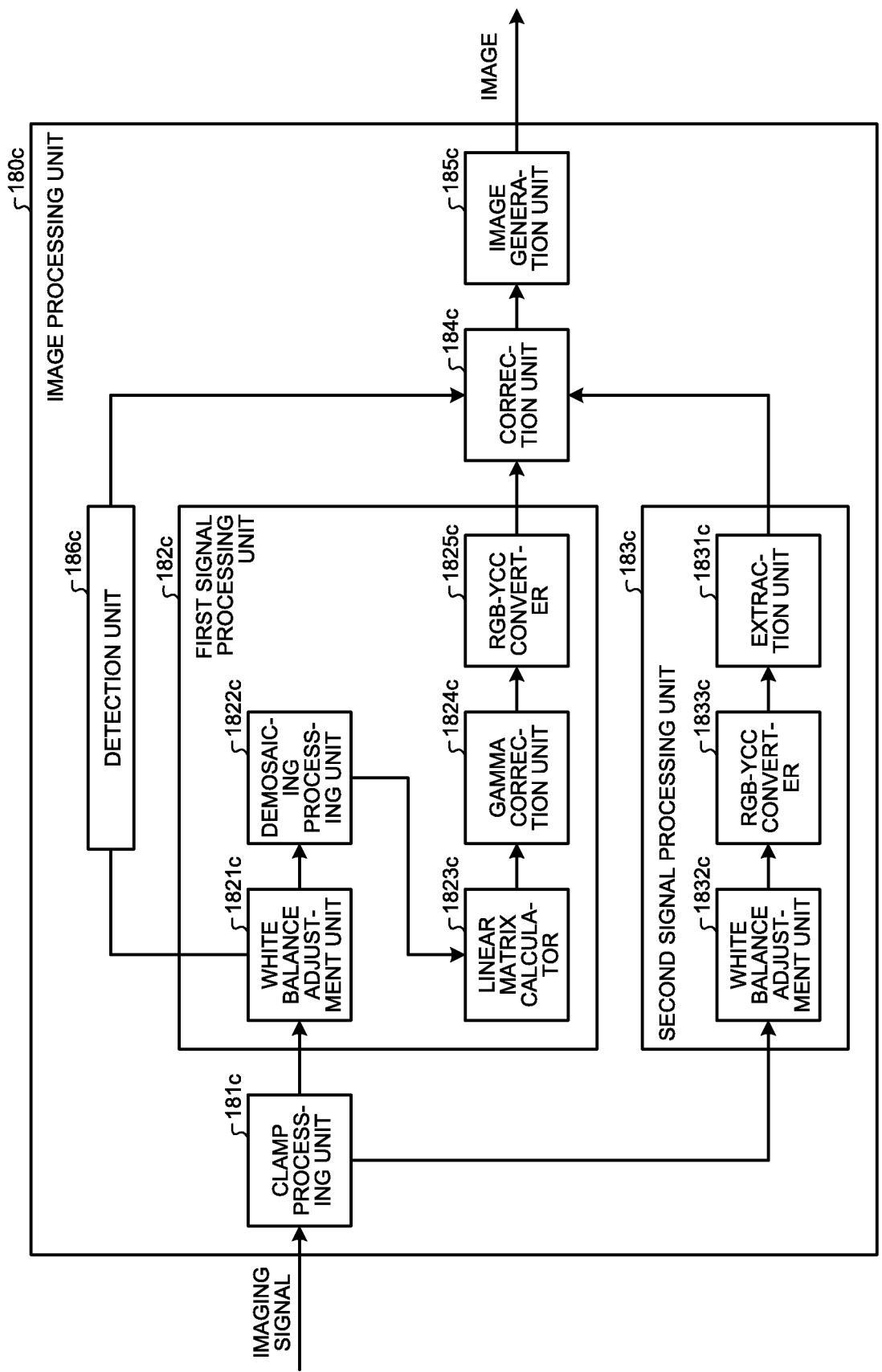
FIG. 10 is a block diagram that illustrates an example of the functional configuration of an image processing unit according to a third embodiment.

The image processing unit according to the second embodiment is described above. Next, the image processing unit according to the third embodiment is described. FIG. 10 is a block diagram that illustrates an example of the functional configuration of an image processing unit 180c according to the third embodiment. In the example described according to the second embodiment, the correction unit 184b applies a detail component to only the area having saturation. According to the third embodiment, a second signal processing unit 183c executes the white balance adjustment on an imaging signal with the gain that is smaller than the gain applied by a first signal processing unit 182c. In the example described, the second signal processing unit 183c extracts a detail component from the luminance signal converted from the saturation signal that is output after the white balance adjustment. The parts different from those in the first embodiment and the second embodiment are described below in detail.

5-1. Functional Configuration of the Image Processing Unit

As illustrated in FIG. 10, the image processing unit 180c includes a clamp processing unit 181c, the first signal processing unit 182c, the second signal processing unit 183c, a correction unit 184c, an image generation unit 185c, and a detection unit 186c.

(1) The Clamp Processing Unit 181c

As the clamp processing unit 181c has the same function as that of the clamp processing unit 181b described in the second embodiment, the detailed description is omitted.

(2) The First Signal Processing Unit 182c

The first signal processing unit 182c has the same function as that of the first signal processing unit 182b described in the second embodiment. As illustrated in FIG. 10, the first signal processing unit 182c includes a white balance adjustment unit 1821c, a demosaicing processing unit 1822c, a linear matrix calculator 1823c, a gamma correction unit 1824c, and an RGB-YCC converter 1825c.

(2-1) The White Balance Adjustment Unit 1821c

As the white balance adjustment unit 1821c has the same function as that of the white balance adjustment unit 1821b described in the second embodiment, the detailed description is omitted.

(2-2) The Demosaicing Processing Unit 1822c

As the demosaicing processing unit 1822c has the same function as those of demosaicing processing units 1822 described in the first embodiment and the second embodiment, the detailed description is omitted.

(2-3) The Linear Matrix Calculator 1823c

As the linear matrix calculator 1823c has the same function as those of linear matrix calculators 1823 described in the first embodiment and the second embodiment, the detailed description is omitted.

(2-4) The Gamma Correction Unit 1824c

As the gamma correction unit 1824c has the same function as those of gamma correction units 1824 described in the first embodiment and the second embodiment, the detailed description is omitted.

(2-5) The RGB-YCC Converter 1825c

As the RGB-YCC converter 1825c has the same function as those of the RGB-YCC converters 1825 described in the first embodiment and the second embodiment, the detailed description is omitted.

(3) The Second Signal Processing Unit 183c

The second signal processing unit 183c is different from the second signal processing units described in the first embodiment and the second embodiment in that the second signal processing unit 183c has the function to covert a saturation signal output after the white balance adjustment from an RGB signal into a luminance signal. The second signal processing unit 183c extracts a detail component from the luminance signal after conversion. As illustrated in FIG. 10, the second signal processing unit 183c includes a white balance adjustment unit 1832c, an RGB-YCC converter 1833c, and an extraction unit 1831c.

(3-1) The White Balance Adjustment Unit 1832c

The white balance adjustment unit 1832c basically has the same function as that of the white balance adjustment unit 1821c in the first signal processing unit 182c. However, the white balance adjustment unit 1832c is different from the white balance adjustment unit 1821c in that the white balance adjustment unit 1832c executes the white balance adjustment on an imaging signal with the gain that is smaller than the gain applied by the white balance adjustment unit 1821c in the first signal processing unit 182c. For example, the white balance adjustment unit 1832c sets the gain such that the signal level after the white balance adjustment does not exceed 100% and then executes the white balance adjustment. This allows the white balance adjustment unit 1832c to output the signal including only the area where no saturation is caused by the white balance adjustment. Hereinafter, the signal including only the area where no saturation is caused by the white balance adjustment is also referred to as an unsaturation signal (third signal).

(3-2) The RGB-YCC Converter 1833c

As the RGB-YCC converter 1833c has the same function as that of the RGB-YCC converter 1825c in the first signal processing unit 182c, the detailed description is omitted.

(3-3) The Extraction Unit 1831c

The extraction unit 1831c basically has the same function as those of extraction units 1831 described in the first embodiment and the second embodiment. However, the extraction unit 1831c is different from the extraction units 1831 according to the first embodiment and the second embodiment in that the extraction unit 1831c extracts a detail component based on an unsaturation signal instead of a saturation signal. Specifically, the extraction unit 1831c extracts a detail component from a luminance signal converted from the unsaturation signal by the RGB-YCC converter 1833c.

(4) The Correction Unit 184c

As the correction unit 184c has the same function as that of the correction unit 184b described in the second embodiment, the detailed description is omitted.

(5) The Image Generation Unit 185c

As the image generation unit 185c has the same function as those of image generation units 185 described in the first embodiment and the second embodiment, the detailed description is omitted.

(6) The Detection Unit 186c

As the detection unit 186c has the same function as that of the detection unit 186b described in the second embodiment, the detailed description is omitted.

5-2. Flow of Image Processing

Figure 11:
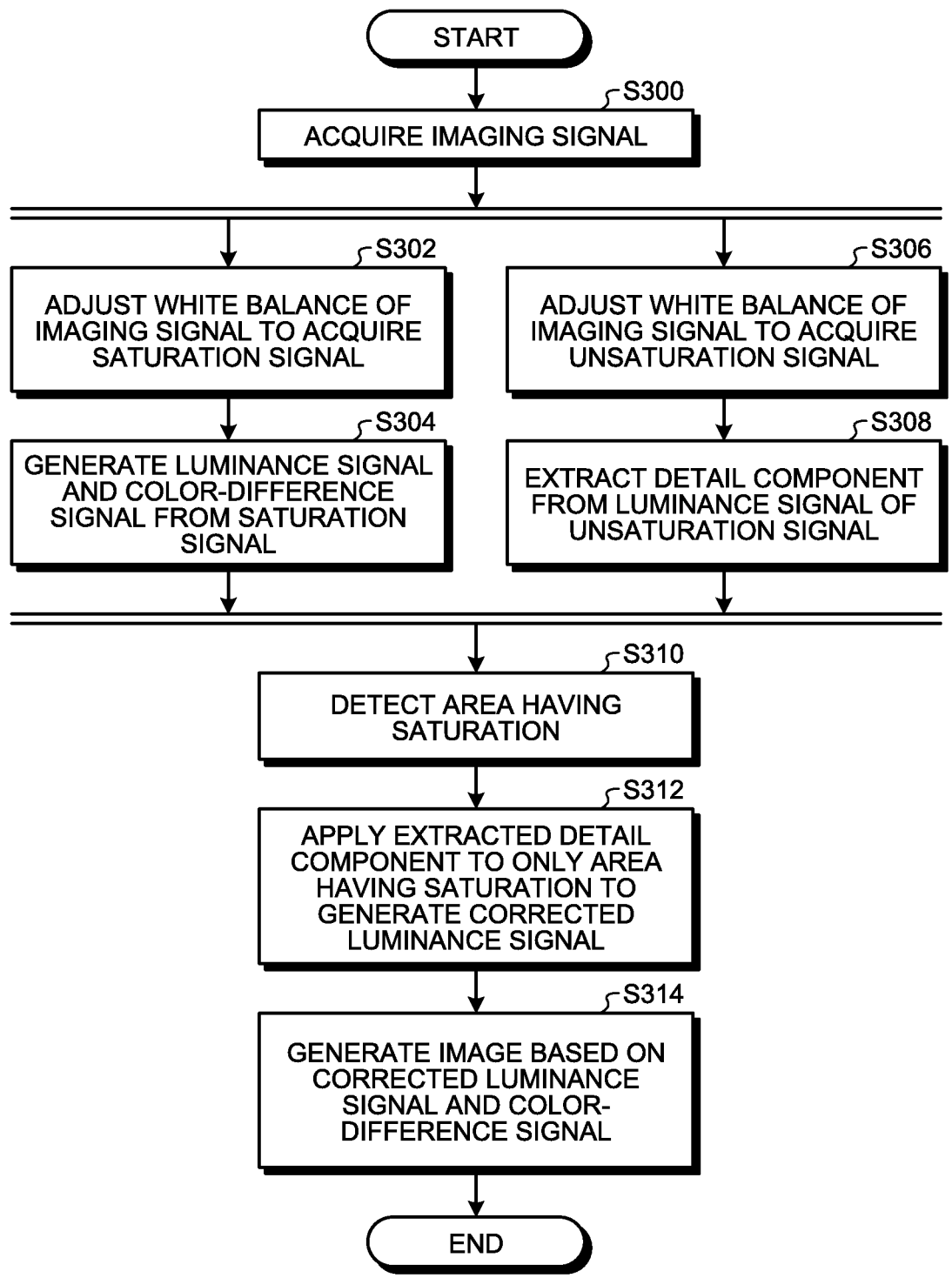
FIG. 11 is a flowchart that illustrates the flow of image processing according to the third embodiment.

FIG. 11 is a flowchart that illustrates the flow of image processing according to the third embodiment. First, the image processing unit 180*c* acquires an imaging signal (S300). Subsequently, the image processing unit 180*c* adjusts the white balance of the imaging signal to acquire a saturation signal (S302). Then, the image processing unit 180*c* generates a luminance signal and a color-difference signal from the acquired saturation signal (S304). In parallel with the operations at S302 and S304, the image processing unit 180*c* adjusts the white balance of the imaging signal to acquire an unsaturation signal (S306). Then, the image processing unit 180*c* extracts a detail component from the luminance signal converted from the unsaturation signal (S308).

The image processing unit 180*c* detects the area having saturation (S310). Subsequently, the image processing unit 180*c* applies the extracted detail component to only the area having saturation in the luminance signal to generate a corrected luminance signal (S312). Then, the image processing unit 180*c* generates an image based on the generated corrected luminance signal and the color-difference signal (S314).

6. An Image Processing Unit According to a Fourth Embodiment

Figure 12:
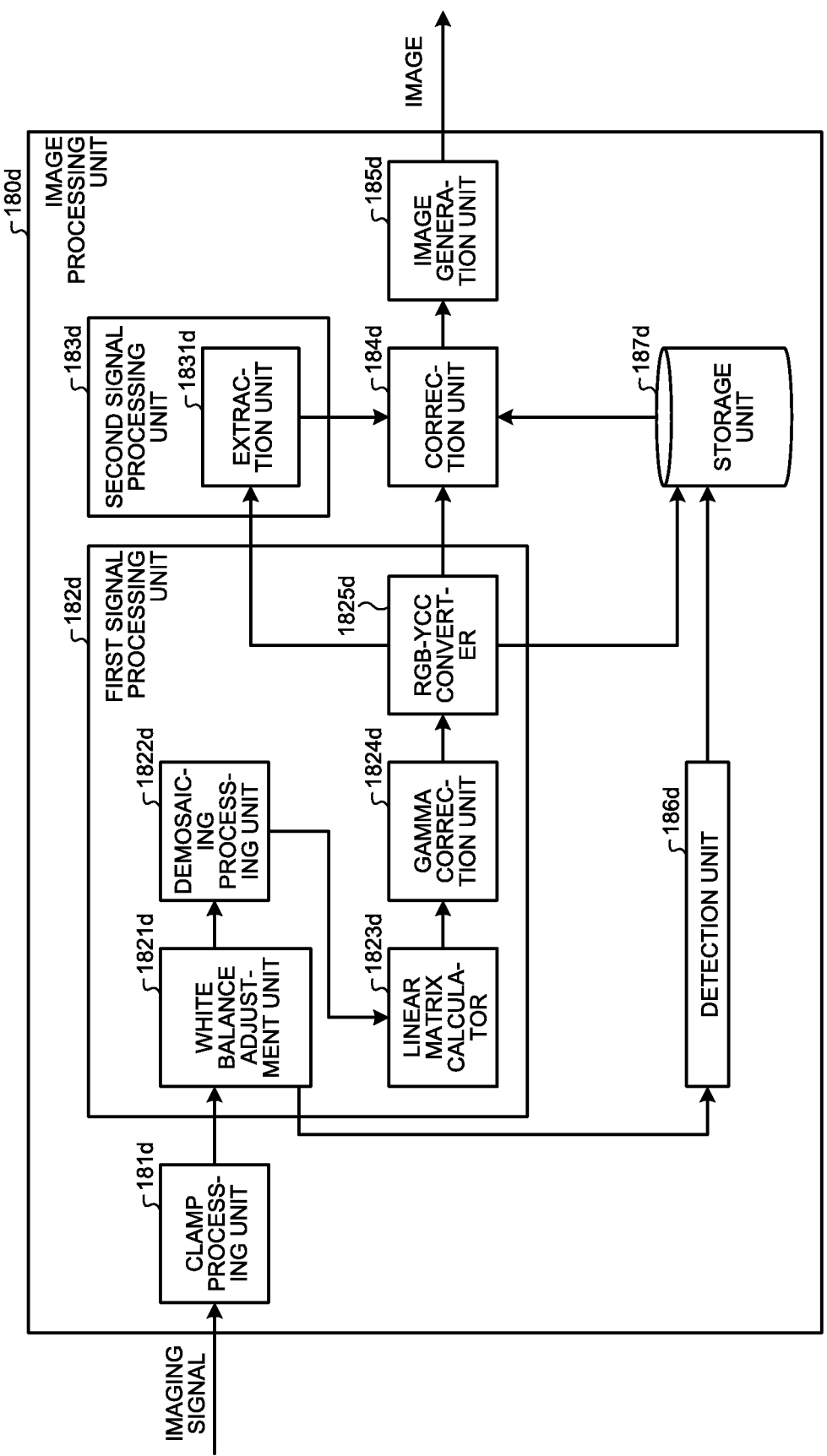
FIG. 12 is a block diagram that illustrates an example of the functional configuration of an image processing unit according to a fourth embodiment.

The image processing unit according to the third embodiment is described above. Next, the image processing unit according to the fourth embodiment is described. FIG. 12 is a block diagram that illustrates an example of the functional configuration of an image processing unit 180*d* according to the fourth embodiment. In the example described according to the first embodiment to the third embodiment, a first signal processing unit 182 and a second signal processing unit 183, which are connected in parallel, perform the signal processing based on the single imaging signal. In the example described according to the fourth embodiment, the first signal processing unit 182 and the second signal processing unit 183, which are connected in series, perform the signal processing based on two temporally different imaging signals.

The image processing unit 180*d* according to the fourth embodiment generates a corrected luminance signal based on two imaging signals that are acquired at different times. For example, the image processing unit 180*d* generates a first luminance signal, which is the target to be corrected, based on a first imaging signal and generates a second luminance signal, which is the target from which a detail component is extracted, based on a second imaging signal. The image processing unit 180*d* applies the detail component extracted from the second luminance signal to the first luminance signal, which is the target to be corrected, to generate a corrected luminance signal. Thus, as the image processing unit 180*d* is configured to perform a time-division process in series, it is possible to generate a corrected luminance signal with the unit having the simpler configuration as compared with the image processing unit 180*c* according to the third embodiment.

6-1. Functional Configuration of the Image Processing Unit

As illustrated in FIG. 12, the image processing unit 180*d* includes a clamp processing unit 181*d*, a first signal processing unit 182*d*, a second signal processing unit 183*d*, a correction unit 184*d*, an image generation unit 185*d*, a detection unit 186*d*, and a storage unit 187*d*.

(1) The Clamp Processing Unit 181*d*

The clamp processing unit 181*d* basically has the same function as those of the clamp processing units 181 described in the first embodiment to the third embodiment. However, the clamp processing unit 181*d* is different from the clamp processing units 181 according to the first embodiment to the third embodiment in that the clamp processing unit 181*d* outputs an imaging signal to only the first signal processing unit 182*d*.

(2) The First Signal Processing Unit 182*d*

The first signal processing unit 182*d* basically has the same function as those of the first signal processing units 182 according to the first embodiment to the third embodiment. However, the first signal processing unit 182*d* is different from the first signal processing units 182 according to the first embodiment to the third embodiment in that the first signal processing unit 182*d* generates two luminance signals based on two temporally different imaging signals. As illustrated in FIG. 12, the first signal processing unit 182*d* includes a white balance adjustment unit 1821*d*, a demosaicing processing unit 1822*d*, a linear matrix calculator 1823*d*, a gamma correction unit 1824*d*, and an RGB-YCC converter 1825*d*.

(2-1) The White Balance Adjustment Unit 1821*d*

As the white balance adjustment unit 1821*d* has the same function as those of white balance adjustment units 1821 described in the second embodiment and the third embodiment, the detailed description is omitted.

(2-2) The Demosaicing Processing Unit 1822*d*

As the demosaicing processing unit 1822*d* has the same function as those of the demosaicing processing units 1822 described in the first embodiment to the third embodiment, the detailed description is omitted.

(2-3) The Linear Matrix Calculator 1823*d*

As the linear matrix calculator 1823*d* has the same function as those of the linear matrix calculators 1823 described in the first embodiment to the third embodiment, the detailed description is omitted.

(2-4) The Gamma Correction Unit 1824*d*

As the gamma correction unit 1824*d* has the same function as those of the gamma correction units 1824 described in the first embodiment to the third embodiment, the detailed description is omitted.

(2-5) The RGB-YCC Converter 1825*d*

The RGB-YCC converter 1825*d* basically has the same function as those of the RGB-YCC converters 1825 described in the first embodiment to the third embodiment. However, the RGB-YCC converter 1825*d* is different from the RGB-YCC converters 1825 according to the first embodiment to the third embodiment in that the RGB-YCC converter 1825*d* outputs the first luminance signal to the storage unit 187*d* and outputs the second luminance signal to an extraction unit 1831*d* in the second signal processing unit 183*d*.

(3) The Second Signal Processing Unit 183*d*

The second signal processing unit 183*d* basically has the same function as those of the second signal processing units 183 described in the first embodiment and the second embodiment. However, the second signal processing unit 183*d* is different from the second signal processing units 183 according to the first embodiment and the second embodiment in that the second signal processing unit 183*d* extracts a detail component from a luminance signal input from the first signal processing unit 182*d*. As illustrated in FIG. 12, the second signal processing unit 183*d* includes the extraction unit 1831*d*.

(3-1) The Extraction Unit 1831*d*

The extraction unit 1831*d* basically has the same function as those of the extraction units 1831 described in the first embodiment and the second embodiment. However, the extraction unit 1831*d* is different from the extraction units 1831 according to the first embodiment and the second embodiment in that the extraction unit 1831d extracts a detail component from a luminance signal input from the RGB-YCC converter 1825d instead of the clamp processing unit 181.

(4) The Correction Unit 184d

The correction unit 184d basically has the same function as those of correction units 184 described in the second embodiment and the third embodiment. However, the correction unit 184d is different from the correction units 184 according to the second embodiment and the third embodiment in that the correction unit 184d applies a detail component input from the extraction unit 1831d to the first luminance signal input from the storage unit 187d on the basis of a detection result input from the storage unit 187d.

(5) The Image Generation Unit 185d

As the image generation unit 185d has the same function as those of the image generation units 185 described in the first embodiment to the third embodiment, the detailed description is omitted.

(6) The Detection Unit 186d

The detection unit 186d basically has the same function as those of the detection units 186 described in the second embodiment and the third embodiment. However, the detection unit 186d is different from the detection units 186 according to the second embodiment and the third embodiment in that the detection unit 186d outputs a detection result of the area having saturation to the storage unit 187d.

(7) The Storage Unit 187d

The storage unit 187d has the function to store data generated by the image processing unit 180d. For example, the storage unit 187d stores the first luminance signal generated by the RGB-YCC converter 1825d in the first signal processing unit 182d. The storage unit 187d outputs the stored first luminance signal to the correction unit 184d as appropriate. The storage unit 187d stores a detection result of the detection unit 186d as to the area having saturation. The storage unit 187d outputs the stored detection result to the correction unit 184d as appropriate.

6-2. Flow of Image Processing

Figure 13:
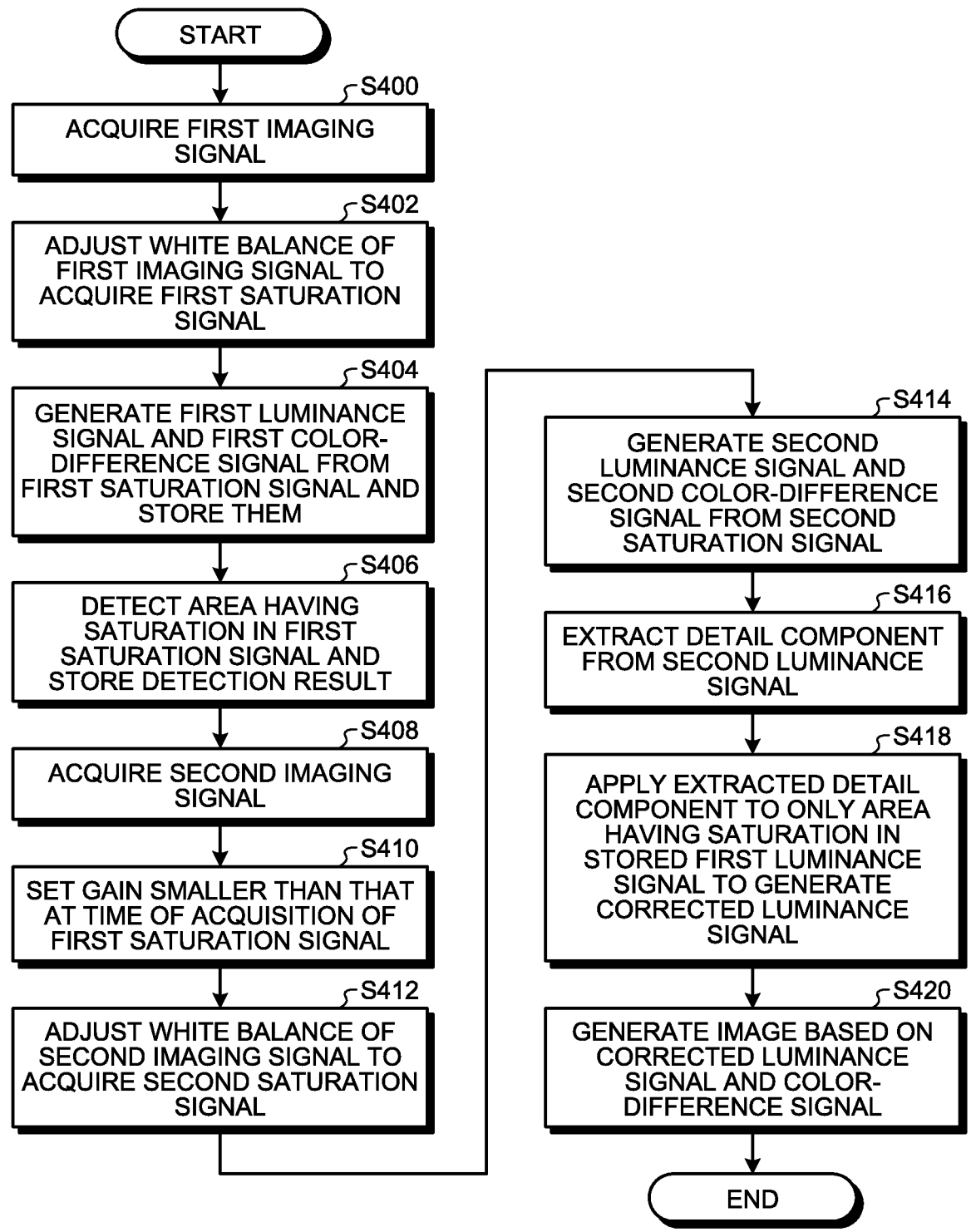
FIG. 13 is a flowchart that illustrates the flow of image processing according to the fourth embodiment.

FIG. 13 is a flowchart that illustrates the flow of image processing according to the fourth embodiment. First, the image processing unit 180d acquires the first imaging signal (S400). Subsequently, the image processing unit 180d adjusts the white balance of the first imaging signal to acquire a first saturation signal (S402). Then, the image processing unit 180d generates the first luminance signal and a first color-difference signal from the acquired first saturation signal and stores them (S404). The image processing unit 180d detects the area having saturation in the acquired first saturation signal and stores a detection result (S406).

After storing the first luminance signal and the first color-difference signal, the image processing unit 180d acquires the second imaging signal different from the first imaging signal (S408). Subsequently, the image processing unit 180d sets the gain that is smaller than that at the time of acquisition of the first saturation signal (S410). Then, the image processing unit 180d adjusts the white balance of the second imaging signal to acquire a second saturation signal (S412). Then, the image processing unit 180d generates the second luminance signal and a second color-difference signal from the second saturation signal (S414). Then, the image processing unit 180d extracts a detail component from the second luminance signal (S416).

The image processing unit 180d applies the extracted detail component to only the area having saturation in the stored first luminance signal on the basis of the stored detection result to generate a corrected luminance signal (S418). Then, the image processing unit 180d generates an image based on the generated corrected luminance signal and the color-difference signal (S420).

6-3. Modification

The image processing unit 180d may be configured such that the storage unit 187d stores the detail component extracted by the extraction unit 1831d. With this configuration, the image processing unit 180d may extract a detail component from the first luminance signal generated based on the first imaging signal and store the extracted detail component in the storage unit 187d. This allows the image processing unit 180d to apply the detail component extracted from the first luminance signal and stored in the storage unit 187d to the luminance signal generated from the second imaging signal to generate a corrected luminance signal.

7. An Image Processing Unit According to a Fifth Embodiment

Figure 14:
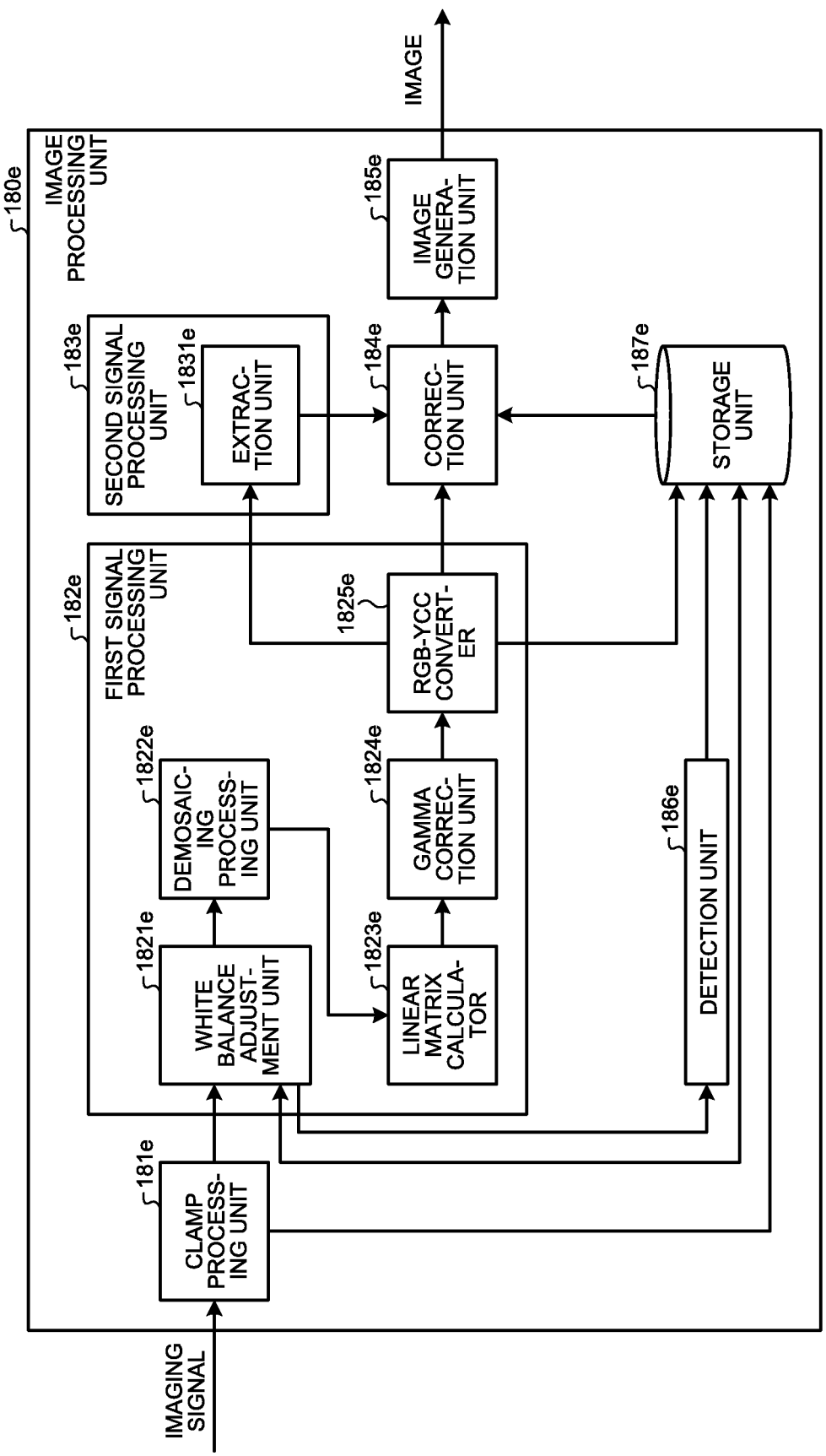
FIG. 14 is a block diagram that illustrates an example of the functional configuration of an image processing unit according to a fifth embodiment.

The image processing unit according to the fourth embodiment is described above. Next, an image processing unit according to a fifth embodiment is described. FIG. 14 is a block diagram that illustrates an example of the functional configuration of an image processing unit 180e according to the fifth embodiment. In the example described according to the fourth embodiment, the first signal processing unit 182 and the second signal processing unit 183, which are connected in series, perform the signal processing based on two temporally different imaging signals. In the example described according to the fifth embodiment, the first signal processing unit 182 and the second signal processing unit 183, which are connected in series, perform the signal processing based on the single imaging signal.

The image processing unit 180e according to the fifth embodiment generates a corrected luminance signal based on the single imaging signal. For example, the image processing unit 180e generates the first luminance signal, which is the target to be corrected, based on the acquired imaging signal. The image processing unit 180e stores the imaging signal at the time of acquisition in a storage unit 187e and, based on the stored imaging signal, generates the second luminance signal that is the target from which a detail component is extracted. The image processing unit 180e applies the detail component extracted from the second luminance signal to the first luminance signal, which is the target to be corrected, to generate a corrected luminance signal. Thus, the image processing unit 180e may generate a corrected luminance signal based on a single imaging signal even when the first signal processing unit 182d and a second signal processing unit 183e are connected in series. This allows the image processing unit 180e to reduce noise caused due to a temporal gap as compared with the image processing unit 180d according to the fourth embodiment.

7-1. Functional Configuration of the Image Processing Unit

As illustrated in FIG. 14, the image processing unit 180e includes a clamp processing unit 181e, a first signal processing unit 182e, a second signal processing unit 183e, a correction unit 184e, an image generation unit 185e, a detection unit 186e, and the storage unit 187e.

(1) The Clamp Processing Unit 181e

The clamp processing unit 181e basically has the same function as those of the clamp processing units 181 described in the first embodiment to the fourth embodiment. However, the clamp processing unit 181e is different from the clamp processing units 181 according to the first embodiment to the fourth embodiment in that the clamp processing unit 181e outputs an imaging signal to the storage unit 187e as well as the first signal processing unit 182e.

(2) The First Signal Processing Unit 182e

The first signal processing unit 182e basically has the same function as that of the first signal processing unit 182d according to the fourth embodiment. However, the first signal processing unit 182e is different from the first signal processing unit 182d according to the fourth embodiment in that the first signal processing unit 182e generates two luminance signals based on an imaging signal input from the clamp processing unit 181e and an imaging signal input from the storage unit 187e. As illustrated in FIG. 14, the first signal processing unit 182e includes a white balance adjustment unit 1821e, a demosaicing processing unit 1822e, a linear matrix calculator 1823e, a gamma correction unit 1824e, and an RGB-YCC converter 1825e.

(2-1) The White Balance Adjustment Unit 1821e

The white balance adjustment unit 1821e basically has the same function as that of the white balance adjustment unit 1821d described in the fourth embodiment. However, the white balance adjustment unit 1821e is different from the white balance adjustment unit 1821d according to the fourth embodiment in that the white balance adjustment unit 1821e executes the white balance adjustment on an imaging signal input from the storage unit 187e as well as the clamp processing unit 181e.

(2-2) The Demosaicing Processing Unit 1822e

As the demosaicing processing unit 1822e has the same function as those of the demosaicing processing units 1822 described in the first embodiment to the fourth embodiment, the detailed description is omitted.

(2-3) The Linear Matrix Calculator 1823e

As the linear matrix calculator 1823e has the same function as those of the linear matrix calculators 1823 described in the first embodiment to the fourth embodiment, the detailed description is omitted.

(2-4) The Gamma Correction Unit 1824e

As the gamma correction unit 1824e has the same function as those of the gamma correction units 1824 described in the first embodiment to the fourth embodiment, the detailed description is omitted.

(2-5) The RGB-YCC Converter 1825e

The RGB-YCC converter 1825e has the same function as that of the RGB-YCC converter 1825d described in the fourth embodiment, the detailed description is omitted.

(3) The Second Signal Processing Unit 183e

As the second signal processing unit 183e has the same function as that of the second signal processing unit 183d described in the fourth embodiment, the detailed description is omitted. As illustrated in FIG. 14, the second signal processing unit 183e includes an extraction unit 1831e.

(3-1) The Extraction Unit 1831e

As the extraction unit 1831e has the same function as that of the extraction unit 1831d described in the fourth embodiment, the detailed description is omitted.

(4) The Correction Unit 184e

As the correction unit 184e has the same function as that of the correction unit 184d described in the fourth embodiment, the detailed description is omitted.

(5) The Image Generation Unit 185e

As the image generation unit 185e has the same function as those of the image generation units 185 described in the first embodiment to the fourth embodiment, the detailed description is omitted.

(6) The Detection Unit 186e

As the detection unit 186e has the same function as that of the detection unit 186d described in the fourth embodiment, the detailed description is omitted.

(7) The Storage Unit 187e

The storage unit 187e basically has the same function as that of the storage unit 187d described in the fourth embodiment. However, the storage unit 187e is different from the storage unit 187d according to the fourth embodiment in that the storage unit 187e receives an imaging signal from the clamp processing unit 181e and outputs an imaging signal to the white balance adjustment unit 1821e.

7-2. Flow of Image Processing

Figure 15:
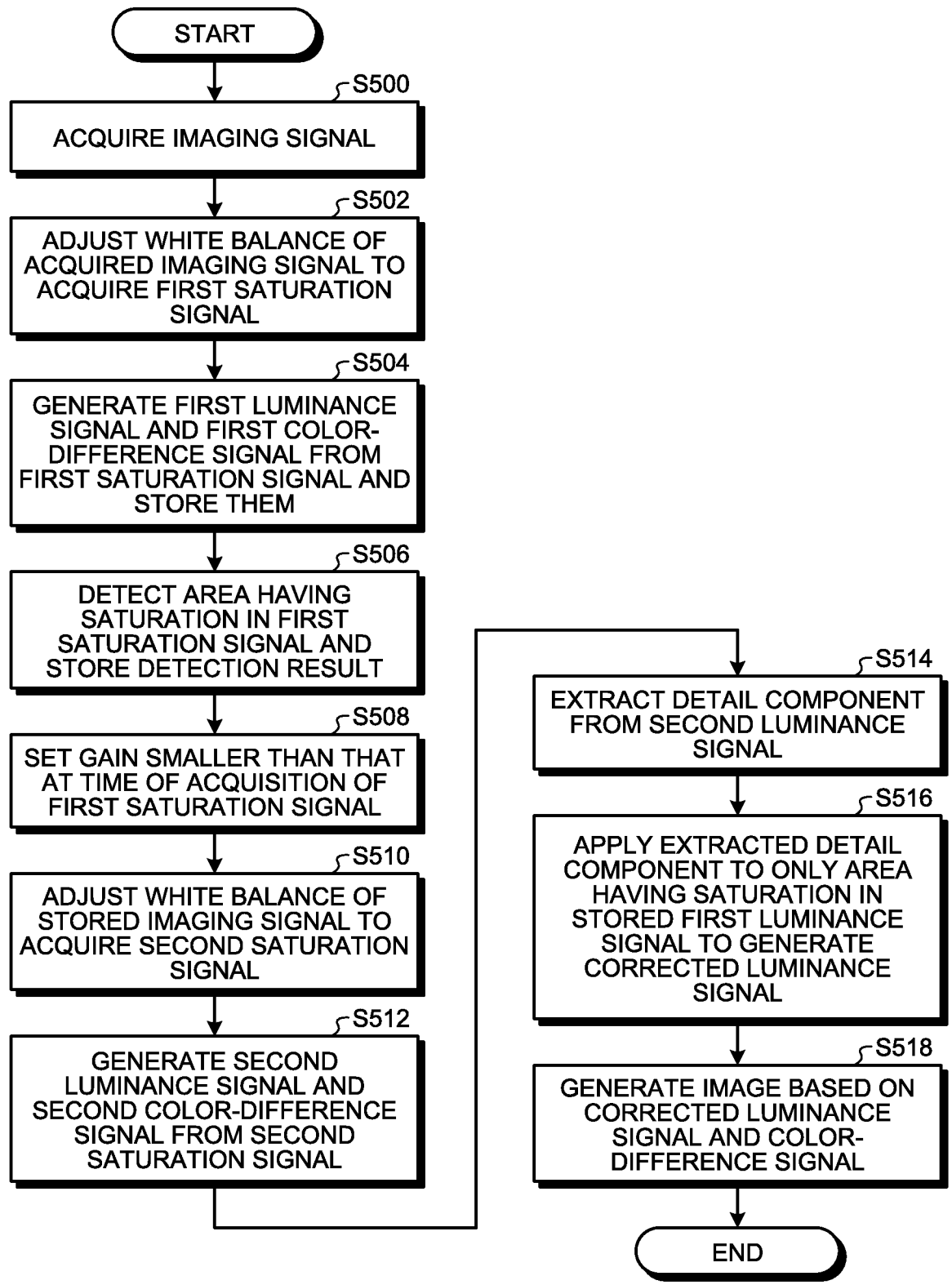
FIG. 15 is a flowchart that illustrates the flow of the image processing according to the fifth embodiment.

FIG. 15 is a flowchart that illustrates the flow of the image processing according to the fifth embodiment. First, the image processing unit 180e acquires an imaging signal (S500). Subsequently, the image processing unit 180e adjusts the white balance of the acquired imaging signal to acquire a first saturation signal (S502). Then, the image processing unit 180e generates the first luminance signal and the first color-difference signal from the first saturation signal and stores them (S504). Then, the image processing unit 180e detects the area having saturation in the acquired first saturation signal and stores a detection result (S506).

After storing the first luminance signal and the first color-difference signal, the image processing unit 180e sets the gain that is smaller than that at the time of acquisition of the first saturation signal (S508). Then, the image processing unit 180e adjusts the white balance of the stored imaging signal to acquire the second saturation signal (S510). Then, the image processing unit 180e generates the second luminance signal and the second color-difference signal from the second saturation signal (S512). Then, the image processing unit 180e extracts a detail component from the second luminance signal (S514).

The image processing unit 180e applies the extracted detail component to only the area having saturation in the stored first luminance signal on the basis of the stored detection result to generate a corrected luminance signal (S516). Then, the image processing unit 180e generates an image based on the generated corrected luminance signal and the color-difference signal (S518).

7-3. Modification

The image processing unit 180e may be configured such that the storage unit 187e stores the detail component extracted by the extraction unit 1831e. With this configuration, the image processing unit 180e may extract a detail component from the first luminance signal generated based on an imaging signal and store the extracted detail component in the storage unit 187e. This allows the image processing unit 180e to apply the detail component stored in the storage unit 187d to the luminance signal generated from the imaging signal to generate a corrected luminance signal.

8. Modification

The embodiments are described above. Next, a modification according to the embodiment is described. The modification described below may be applied instead of the configurations described in the embodiments or may be applied in addition to the configurations described in the embodiments.

In the example described according to the second embodiment to the fifth embodiment described above, a saturation signal is generated due to the white balance adjustment on an imaging signal by the first signal processing unit 182. However, according to the second embodiment to the fifth embodiment described above, an unsaturation signal may be generated due to the white balance adjustment on an imaging signal by the first signal processing unit 182. When the first signal processing unit 182 generates an unsaturation signal, the detection unit 186, to which the unsaturation signal is input, is not able to detect the area having saturation. In this case, the image processing unit 180 may omit the process to generate a corrected luminance signal. The image processing unit 180 may generate an image based on the luminance signal converted from an unsaturation signal.

This allows the image processing unit 180 to omit a process as appropriate and therefore improve the efficiency of the image processing. Furthermore, by omitting a process as appropriate, the image processing unit 180 may also reduce the power consumption.

9. Example of the Hardware Configuration

Figure 16:
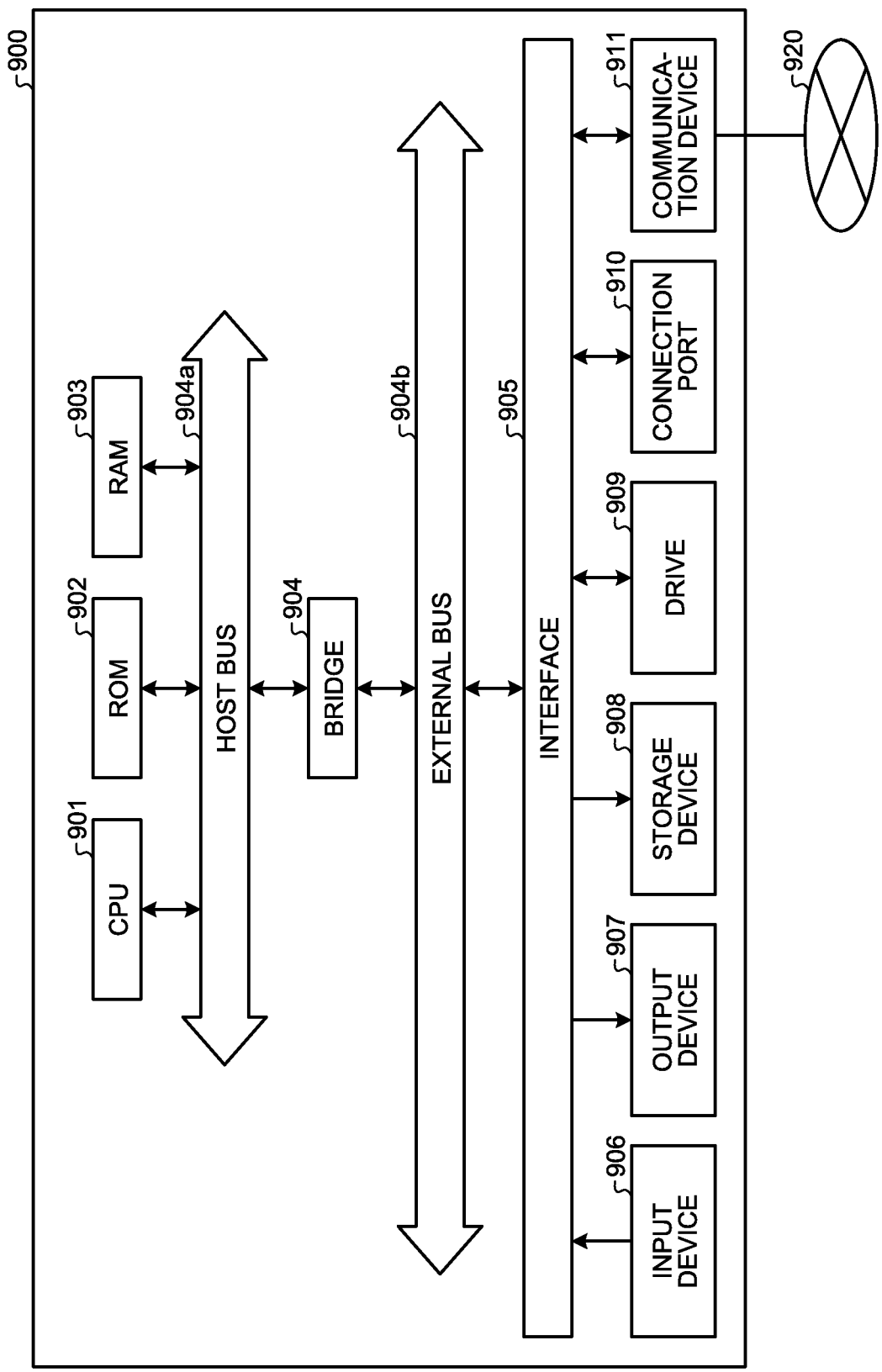
FIG. 16 is a block diagram that illustrates an example of the hardware configuration of an image processing apparatus according to an embodiment.

Finally, with reference to FIG. 16, an example of the hardware configuration of an image processing apparatus according to an embodiment is described. FIG. 16 is a block diagram that illustrates an example of the hardware configuration of the image processing apparatus according to the embodiment. For example, the medical observation device 100 illustrated in FIGS. 1, 3, and 4 may be implemented by using an image processing apparatus 900 illustrated in FIG. 16. The image processing of the image processing apparatus 900 according to the present embodiment is implemented by using software in cooperation with the hardware described below.

As illustrated in FIG. 16, the image processing apparatus 900 includes a central processing unit (CPU) 901, a read only memory (ROM) 902, and a random access memory (RAM) 903. The image processing apparatus 900 further includes a host bus 904a, a bridge 904, an external bus 904b, an interface 905, an input device 906, an output device 907, a storage device 908, a drive 909, a connection port 910, and a communication device 911. The hardware configuration described here is an example, and a part of the components may be omitted. The hardware configuration may further include a component other than the components described here.

The CPU 901 functions as, for example, an arithmetic processing device or a control device to control all or part of the operation of each component based on various programs stored in the ROM 902, the RAM 903, or the storage device 908. The ROM 902 is a unit that stores programs loaded into the CPU 901, data used for calculations, and the like. The RAM 903 temporarily or permanently stores, for example, programs loaded into the CPU 901 and various parameters that are changed as appropriate when the program is executed. They are coupled to one another via the host bus 904a that includes a CPU bus, or the like. The CPU 901, the ROM 902, and the RAM 903, for example, in cooperation with software, may implement the functions of the control device (not illustrated) in the medical observation device 100 described with reference to FIG. 1, the control unit 144 described with reference to FIG. 3, and the control unit 160 described with reference to FIG. 4.

For example, the CPU 901, the ROM 902, and the RAM 903 are coupled to one another via the host bus 904a that enables high-speed data transmission. Conversely, the host bus 904a is coupled to the external bus 904b having a relatively low data transmission speed via, for example, the bridge 904. The external bus 904b is coupled to various components via the interface 905.

The input device 906 is implemented by using a device for inputting information by a user, e.g., a mouse, a keyboard, a touch panel, a button, a microphone, a switch, or a lever. The input device 906 may be a remote control device that uses, for example, infrared rays or other radio waves or may be an external connection device, such as a mobile phone or a PDA, which is compatible with the operation of the image processing apparatus 900. The input device 906 may include an input control circuitry, or the like, which generates an input signal based on the information input by the user using the above-described input unit and outputs it to the CPU 901. The user of the image processing apparatus 900 operates the input device 906 so as to input various types of data to the image processing apparatus 900 and instruct a processing operation.

The input device 906 may be configured by using a device that detects the information about a user. For example, the input device 906 may include various sensors such as an image sensor (e.g., camera), a depth sensor (e.g., stereo camera), an acceleration sensor, a gyroscope, an earth magnetism sensor, an optical sensor, a sound sensor, a distance measuring sensor (e.g., Time of Flight (ToF) sensor), or a force sensor. The input device 906 may acquire the information about the status of the image processing apparatus 900, such as the posture, the moving velocity, or the like, of the image processing apparatus 900, or the information about the surrounding environment of the image processing apparatus 900, such as the brightness, noise, or the like, around the image processing apparatus 900. The input device 906 may include a global navigation satellite system (GNSS) module that receives a GNSS signal from a satellite in the GNSS (e.g., a Global Positioning System (GPS) signal from a satellite in the GPS) to measure the positional information including the latitude, the longitude, and the altitude of the apparatus. With regard to the positional information, the input device 906 may detect the position based on the transmission and reception, short-range communication, etc. with Wi-Fi (registered trademark), a mobile phone, a PHS, a smartphone, or the like. The input device 906 may implement the functions of, for example, the imaging device 106 described with reference to FIG. 1, the imaging device including the insertion member 134, the light source unit 136, and the camera head 140 described with reference to FIG. 3, and the imaging unit 150 described with reference to FIG. 4.

The output device 907 is configured by using a device that is capable of notifying the user of the acquired information in a visual or auditory manner. The device includes a display device, such as a CRT display device, a liquid crystal display device, a plasma display device, an EL display device, a laser projector, an LED projector, or a lamp, a sound output device, such as a speaker or a headphone, or a printer device. The output device 907 outputs, for example, results obtained during various types of processing performed by the image processing apparatus 900. Specifically, the display device visually displays results obtained during various types of processing performed by the image processing apparatus 900 in various formats, such as text, image, chart, or graph. The sound output device converts audio signals including regenerated voice data, sound data, etc. into analog signals and outputs them in an auditory manner.

The storage device 908 is a data storage device that is configured as an example of the storage unit in the image processing apparatus 900. The storage device 908 is implemented by using, for example, a magnetic storage device such as an HDD, a semiconductor storage device, an optical storage device, or a magnetooptical storage device. The storage device 908 may include a storage medium, a recording device that records data in a storage medium, a reading device that reads data from a storage medium, a deletion device that deletes data recorded in a storage medium, etc. The storage device 908 stores programs and various types of data executed by the CPU 901, various types of data acquired from an external unit, etc.

The drive 909 is a reader/writer for a storage medium and is built in or externally coupled to the image processing apparatus 900. The drive 909 reads the information recorded in the removably attached storage medium, such as a magnetic disk, an optical disk, a magnetic optical disk, or a semiconductor memory, and outputs it to the RAM 903. The drive 909 may also write information in the removable storage medium.

The connection port 910 is a port for coupling an externally coupled device, for example, a universal serial bus (USB) port, an IEEE 1394 port, a small computer system interface (SCSI), an RS-232C port, or an optical audio terminal.

The communication device 911 is, for example, a communication interface that is configured by using a communication device, or the like, for connecting to a network 920. The communication device 911 is, for example, a communication card for a wired or wireless local area network (LAN), Long Term Evolution (LTE), Bluetooth (registered trademark), or Wireless USB (WUSB). The communication device 911 may be an optical communication router, an Asymmetric Digital Subscriber Line (ADSL) router, a modem for various types of communications, etc. The communication device 911 may transmit and receive signals, and the like, to and from for example the Internet or other communication devices in accordance with a predetermined protocol such as TCP/IP. The communication device 911 may implement the function of, for example, the communication unit 195 described with reference to FIG. 4.

The network 920 is a wired or wireless transmission path for the information transmitted from an apparatus connected to the network 920. For example, the network 920 may include a public network such as the Internet, a phone network, or a satellite communication network, or various types of local area network (LAN) including Ethernet (registered trademark), or wide area network (WAN). The network 920 may include a dedicated network such as Internet Protocol-Virtual Private Network (IP-VPN).

An example of the hardware configuration that may implement the function of the image processing apparatus 900 according to the present embodiment is described above. Each of the above-described components may be implemented by using a general-purpose member or may be implemented by using the hardware specialized for the function of each component. Therefore, the hardware configuration to be used may be changed as appropriate in accordance with the appropriate technical level for implementing the present embodiment.

10. Conclusion

As described above, the image processing apparatus according to the embodiment executes the white balance adjustment on an imaging signal corresponding to multiple wavelength bands. The image processing apparatus generates a luminance signal from the saturation signal including the area having saturation caused by the adjustment on the white balance. The image processing apparatus extracts a detail component based on the imaging signal. The image processing apparatus applies the detail component to the luminance signal to generate a corrected luminance signal.

As described above, the image processing apparatus applies the detail component extracted from the imaging signal having no saturation to the luminance signal including the area having saturation so as to restore the lost detail in the area having saturation.

Thus, it is possible to provide the image processing apparatus and the observation system that are new and improved so as to make it possible to restore the detail of the area having saturation.

Although preferred embodiments are described above in detail with reference to the accompanying drawings, the technical range is not limited to the examples. It is obvious that a person skilled in the art may arrive at various modifications and changes within the range of the technical idea described in claims, and it is understood that they also belong to the technical range.

For example, each of the devices in the description may be implemented as a single device, or part or all thereof may be implemented as a separate device. For example, at least any one of the imaging unit 150 and the control unit 160 included in the medical observation device 100 illustrated in FIG. 4 may be implemented as a single device. For example, the imaging unit 150 may be configured as an independent device, such as a sensor device, and connected to the medical observation device 100 via a network, etc. The control unit 160 may be configured as an independent device, such as a server device, and connected to the medical observation device 100 via a network, etc.

The series of processes performed by each device in the description may be implemented by using any one of software, hardware, and the combination of software and hardware. A program included in the software is previously stored in, for example, a recording medium (non-transitory media) provided inside or outside each device. Each program is loaded into a RAM when it is executed by, for example, the computer and is executed by a processor, such as a CPU.

The processes in the description with reference to the flowcharts may be executed in an order different from the order illustrated. Some of the processing steps may be performed in parallel. An additional processing step may be adopted, and a part of the processing steps may be omitted.

The advantageous effect in the description is for purposes of explanation or illustration and not limitation. That is, the technique according to the present disclosure may produce other advantageous effects that are obvious to a person skilled in the art from the description in addition to the above-described advantageous effect or instead of the above-described advantageous effect.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:
1. An image processing apparatus comprising
 a processor comprising hardware, the processor being configured to:
  execute a first white balance adjustment on a first signal corresponding to multiple wavelength bands on a target;
  generate a first luminance signal from a second signal including an area having saturation caused by the first white balance adjustment;

extract a detail component based on the first signal, wherein the detail component includes information regarding the target before the first white balance adjustment is executed;

generate a second luminance signal using the detail component and the first luminance signal, wherein the second luminance signal is a corrected luminance signal; and apply the detail component only to the area having the saturation to the luminance signal to generate the corrected luminance signal.

2. The image processing apparatus according to claim 1, wherein the processor is configured to detect the area having the saturation based on a threshold process on the wavelength bands corresponding to the second signal.

3. The image processing apparatus according to claim 2, wherein the processor is configured to detect that an area corresponding to the wavelength bands is the area having the saturation when a difference between a highest pixel value and a second highest pixel value among pixel values corresponding to the respective wavelength bands is more than a predetermined threshold.

4. The image processing apparatus according to claim 1, wherein the processor is configured to detect at least one of a red wavelength band, a green wavelength band, and a blue wavelength band as a wavelength band in which the saturation has occurred.

5. The image processing apparatus according to claim 4, wherein the processor is configured to detect that the red wavelength band is the wavelength band in which the saturation has occurred.

6. The image processing apparatus according to claim 1, wherein the processor is configured to add the detail component to the luminance signal at a predetermined ratio to generate the corrected luminance signal.

7. The image processing apparatus according to claim 6, wherein the processor is configured to adjust a signal level of the corrected luminance signal so as to be decreased.

8. The image processing apparatus according to claim 1, wherein the processor is configured to extract the detail component from the first signal by using a high-pass filter.

9. The image processing apparatus according to claim 1, wherein the processor is configured to: execute second white balance adjustment on the first signal with a gain that is smaller than a gain applied by the first white balance adjustment; and extract the detail component based on a third signal including only an area having no saturation caused by the second white balance adjustment.

10. The image processing apparatus according to claim 1, wherein the processor is further configured to: generate a color-difference signal from the second signal; and generate an image based on the color-difference signal and the corrected luminance signal.

11. The image processing apparatus according to claim 1, wherein the processor is further configured to apply a same detail component to the first luminance signal.

* * * * *